United States Patent
Ding

(10) Patent No.: US 10,914,731 B2
(45) Date of Patent: Feb. 9, 2021

(54) METHOD OF REMOVING NON-SPECIFIC BINDING SIGNALS USING MICROPARTICLE ASSAY

(71) Applicant: Qinxue Ding, Mountain View, CA (US)

(72) Inventor: Qinxue Ding, Mountain View, CA (US)

(73) Assignee: Qinxue Ding, Sunnyvale, CA (US)

( * ) Notice: Subject to any disclaimer, the term of this patent is extended or adjusted under 35 U.S.C. 154(b) by 0 days.

(21) Appl. No.: 16/797,149

(22) Filed: Feb. 21, 2020

(65) Prior Publication Data

US 2020/0271645 A1    Aug. 27, 2020

Related U.S. Application Data

(60) Provisional application No. 62/808,746, filed on Feb. 21, 2019.

(51) Int. Cl.
*G01N 33/543* (2006.01)
*G01N 33/58* (2006.01)
(Continued)

(52) U.S. Cl.
CPC ....... *G01N 33/54313* (2013.01); *G01N 15/14* (2013.01); *G01N 33/582* (2013.01);
(Continued)

(58) Field of Classification Search
CPC .......... G01N 33/54313; G01N 33/582; G01N 33/686; G01N 15/14; G01N 2015/1006; G01N 2015/0065
See application file for complete search history.

(56) References Cited

U.S. PATENT DOCUMENTS 5,585,241 A * 12/1996 Lindmo ............. G01N 15/14
                                                     435/6.11
5,723,346 A *  3/1998 Frengen .......... G01N 33/54313
                                                     436/523

(Continued)

OTHER PUBLICATIONS

International Search Report and Written Opinion on PCT/US2020/019159, dated May 7, 2020.

*Primary Examiner* — Gailene Gabel
(74) *Attorney, Agent, or Firm* — Yong Chen; Lin Sun-Hoffman; Liu Chen & Hoffman LLP

(57) ABSTRACT

Methods and kits for accurately detecting one or more analytes in a sample by removing non-specific binding signals utilizing capture and control microparticles. The capture microparticles can specifically bind to the analyte while the control microparticles do not specifically bind to the analyte but to the background molecules. Both capture and control microparticles are added to the sample under suitable conditions to allow binding between analytes and the microparticles. Detection agent is then added to bind to analytes and other substances captured by the microparticles. The microparticles are then run through a cytometry-based detection method, where detection signals from the capture and the control microparticles are distinguished. The differences between the detection signals from the capture and the control microparticles are obtained, which are then used to determine the presence and/or amounts of the analytes based on a previously determined relationship between such differences and known amount of the analyte.

23 Claims, 38 Drawing Sheets

(51) Int. Cl.
*G01N 15/14* (2006.01)
*G01N 33/68* (2006.01)
*G01N 15/10* (2006.01)
*G01N 15/00* (2006.01)

(52) U.S. Cl.
CPC ... *G01N 33/686* (2013.01); *G01N 2015/0065* (2013.01); *G01N 2015/1006* (2013.01)

(56) References Cited

U.S. PATENT DOCUMENTS

| | | |
|---|---|---|
| 6,268,222 B1 | 7/2001 | Chandler et al. |
| 2006/0292552 A1 | 12/2006 | Haquette et al. |
| 2011/0183363 A1 | 7/2011 | Fischer et al. |
| 2013/0115621 A1* | 5/2013 | Parhami-Seren ...... C07K 16/40 435/7.5 |
| 2013/0344621 A1* | 12/2013 | Wang ................ G01N 33/6854 436/501 |
| 2016/0231328 A1 | 8/2016 | Krishna et al. |
| 2018/0088112 A1 | 3/2018 | Fan et al. |
| 2018/0180601 A1* | 6/2018 | Pedersen .......... G01N 33/56977 |
| 2019/0331689 A1* | 10/2019 | Mei ................ G01N 33/56972 |

* cited by examiner

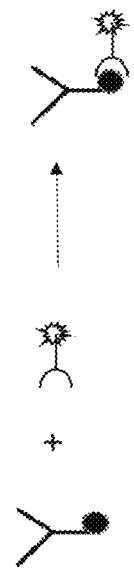
Fig. 2C
where ⚬⚙ is a detection agent
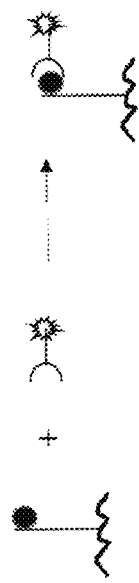
Fig. 2D

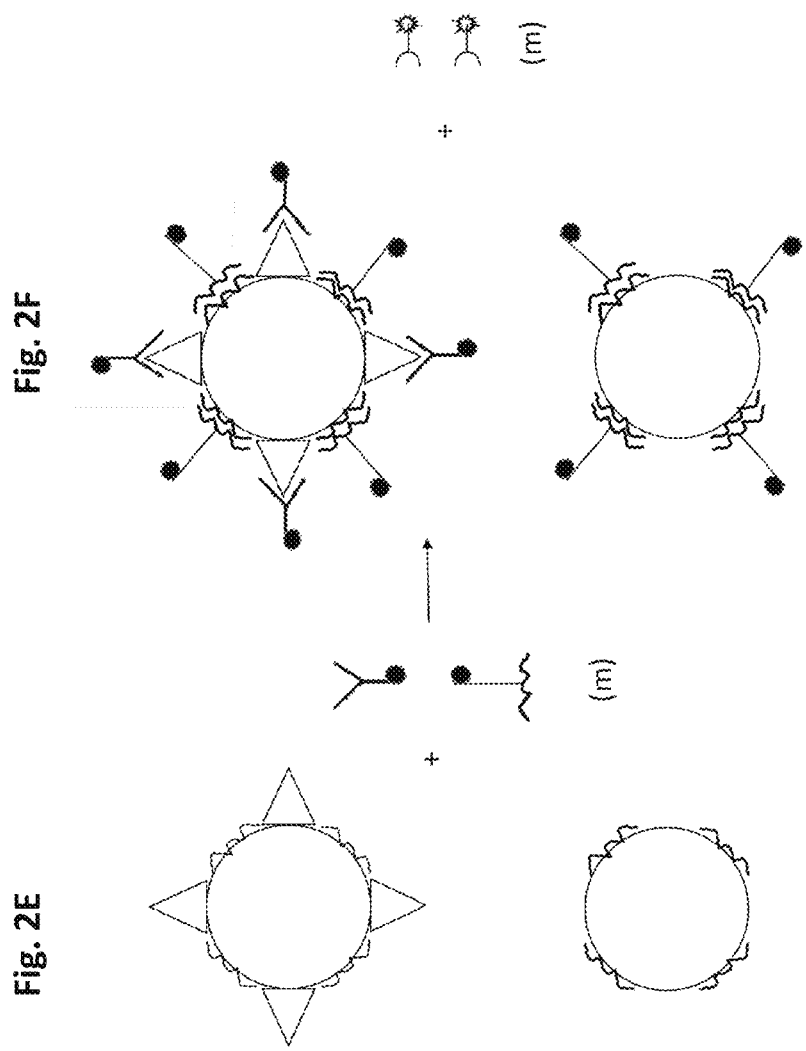

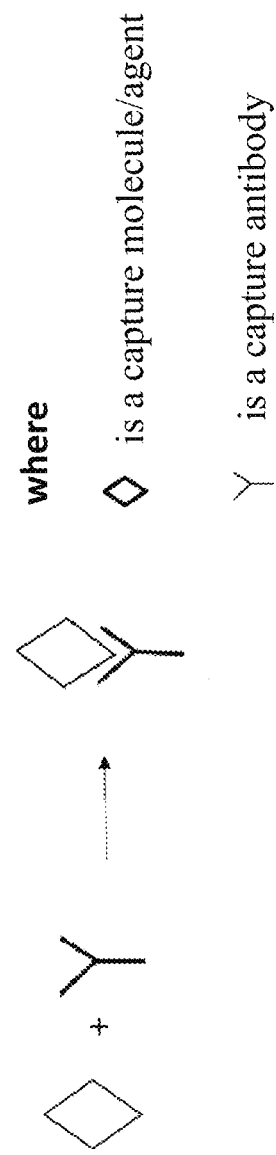
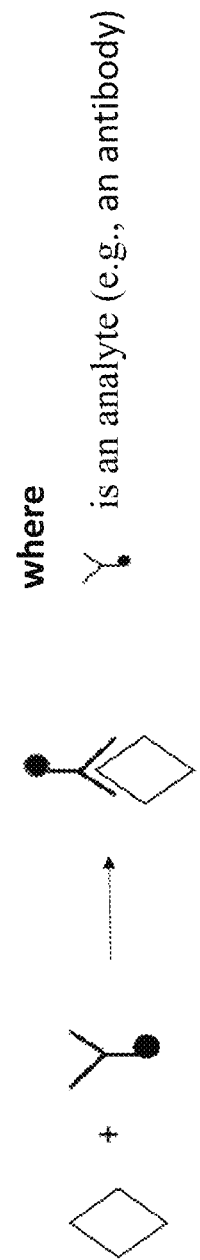

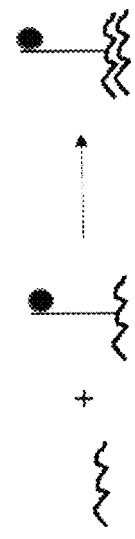

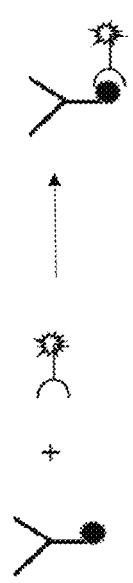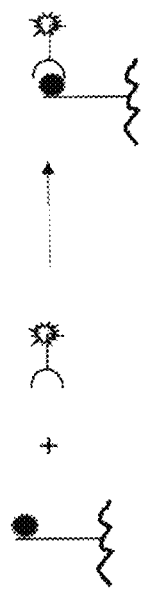

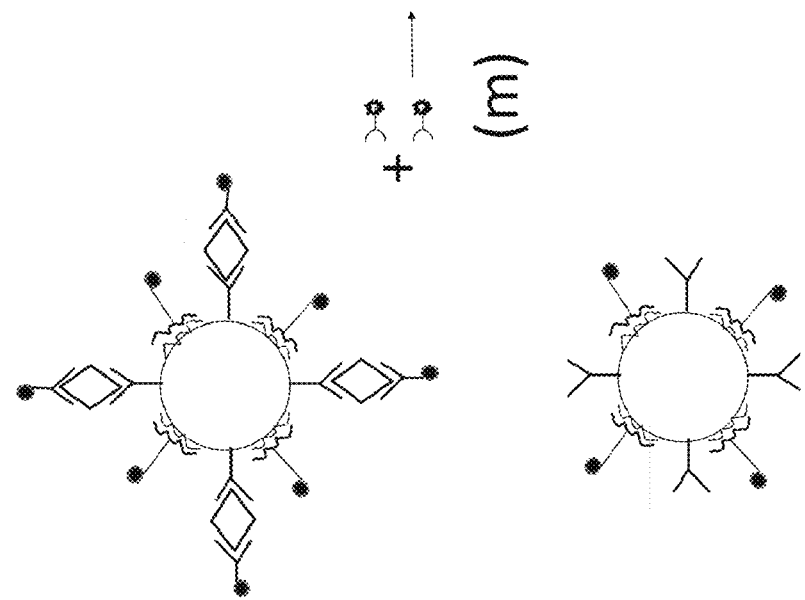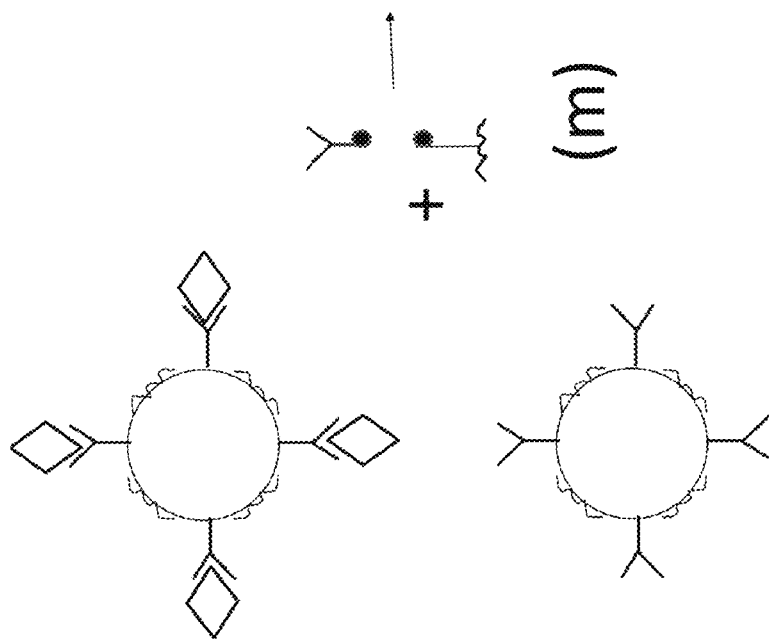

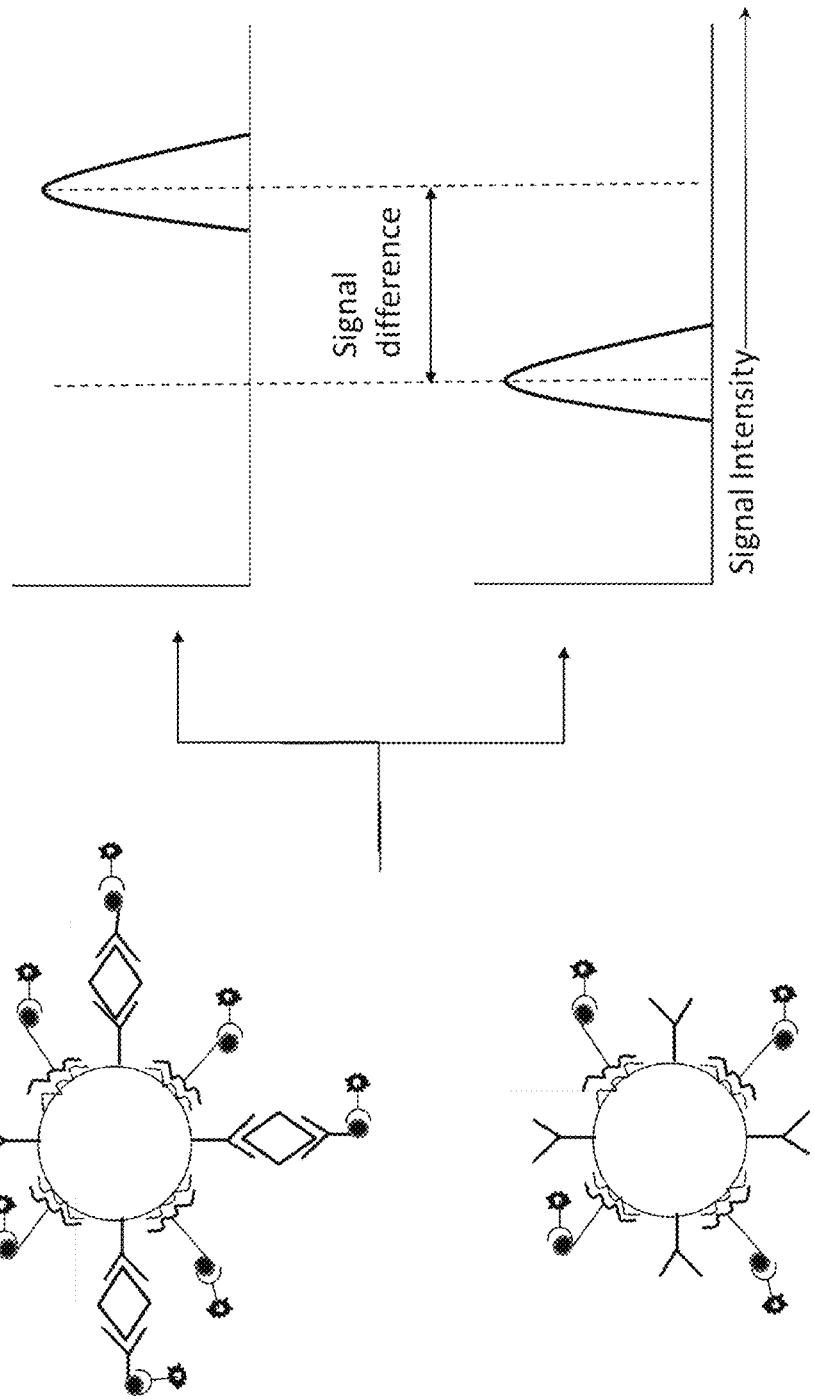

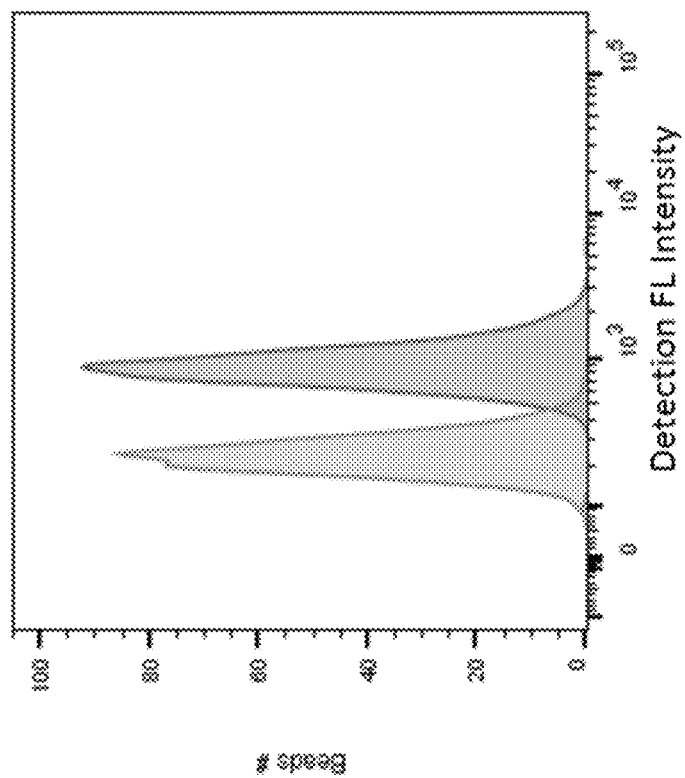

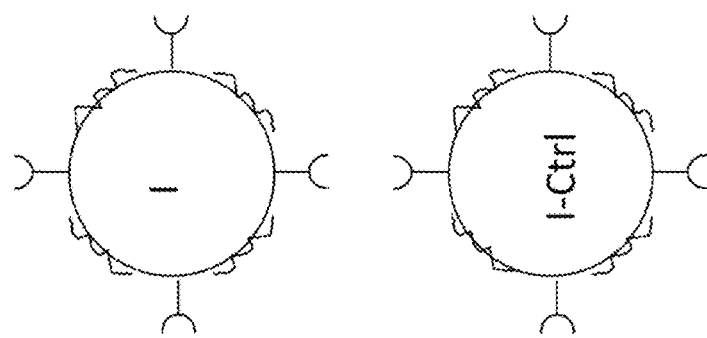

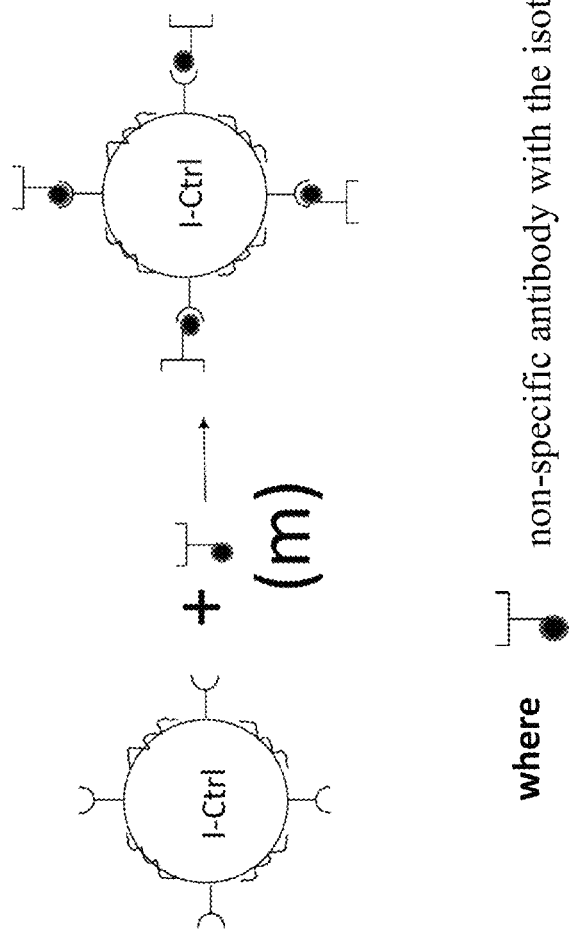

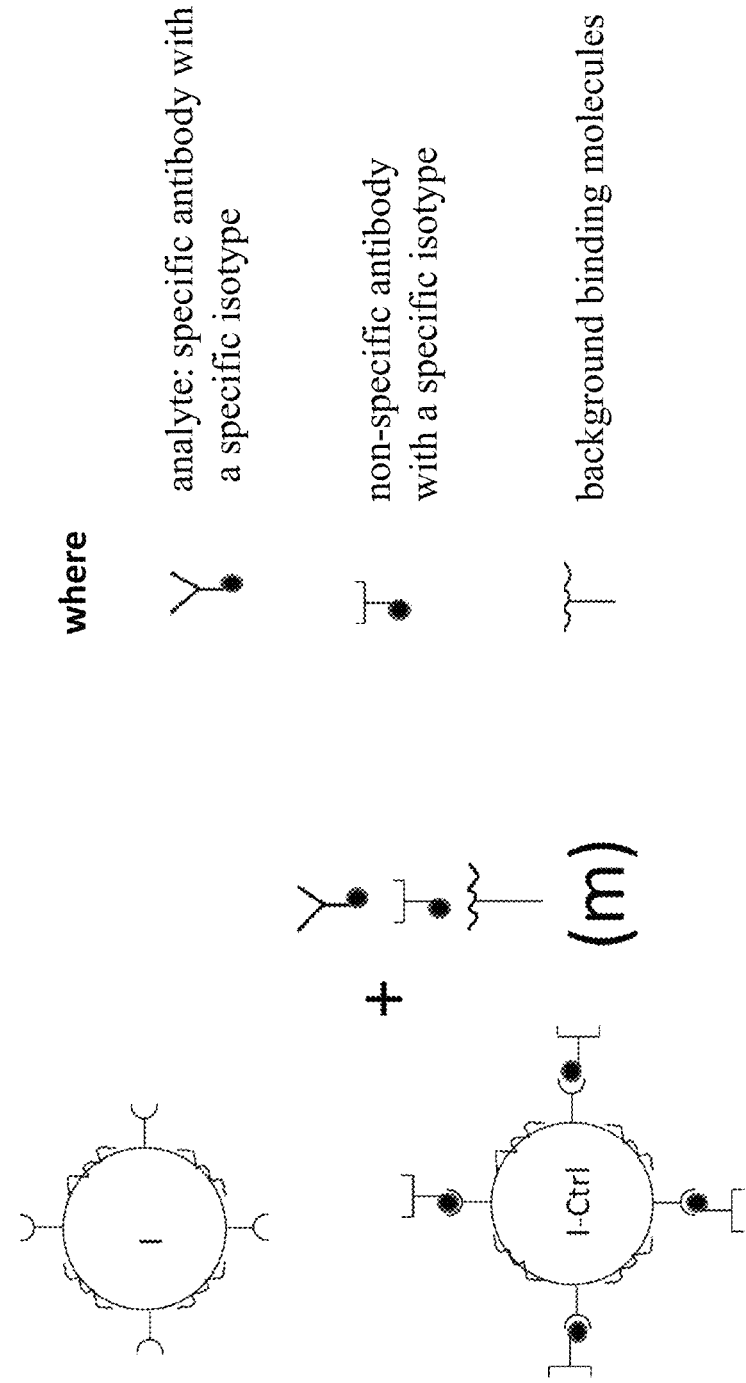

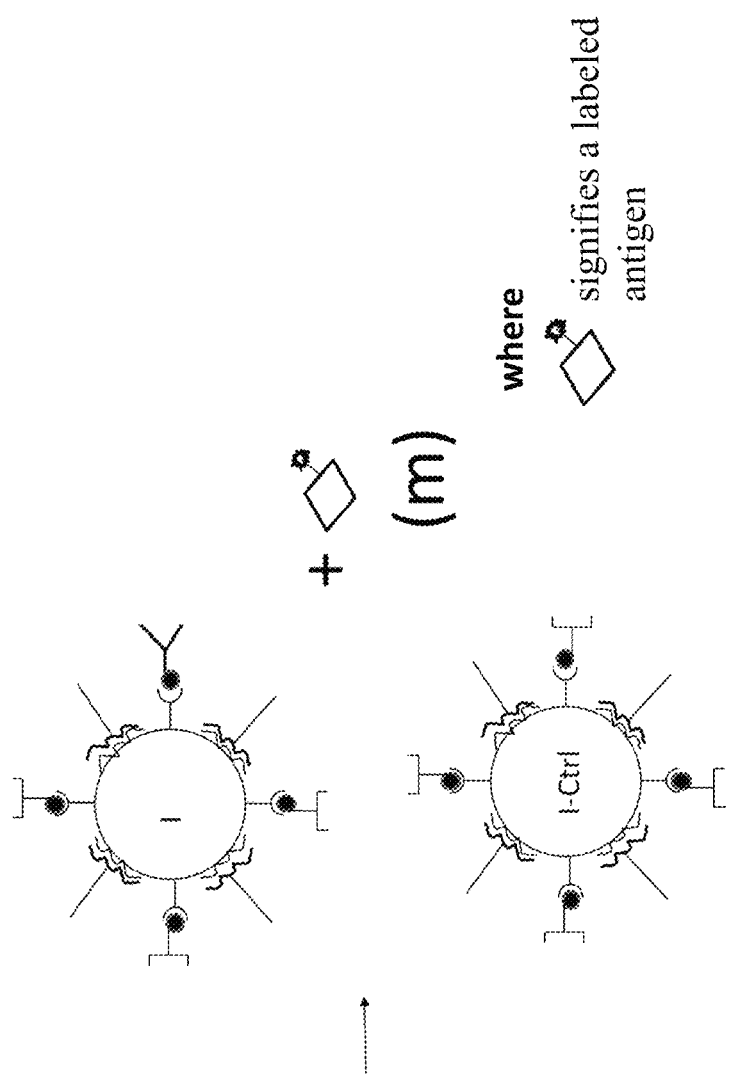

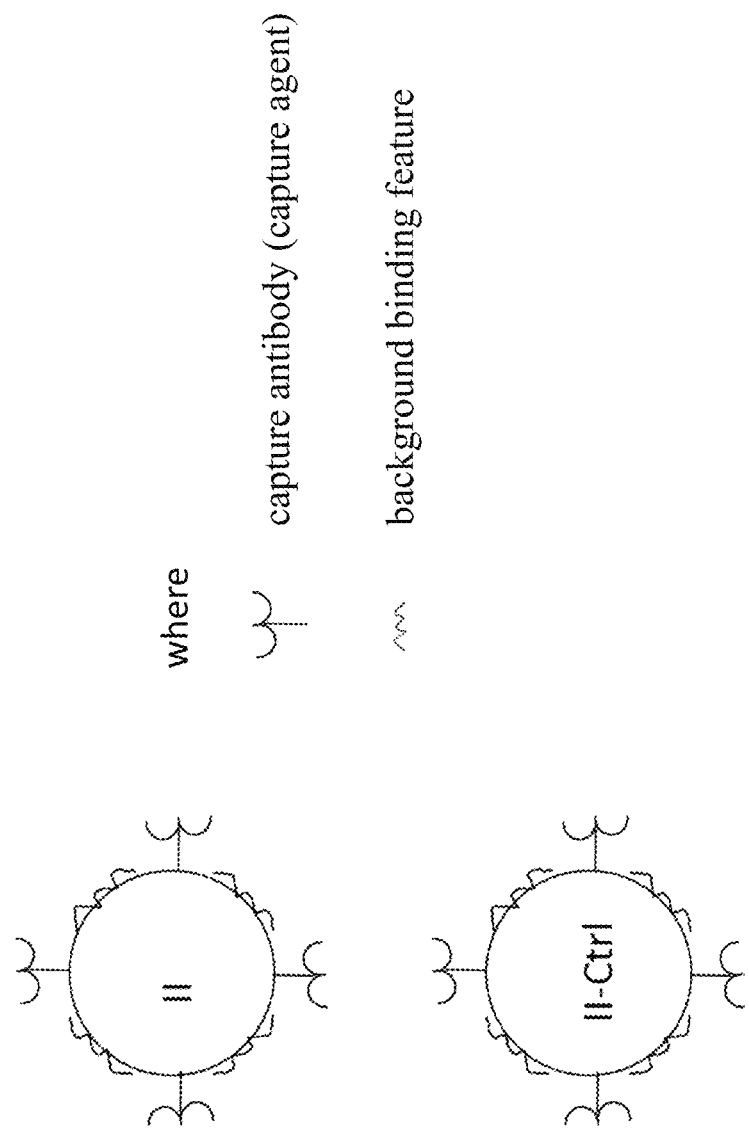

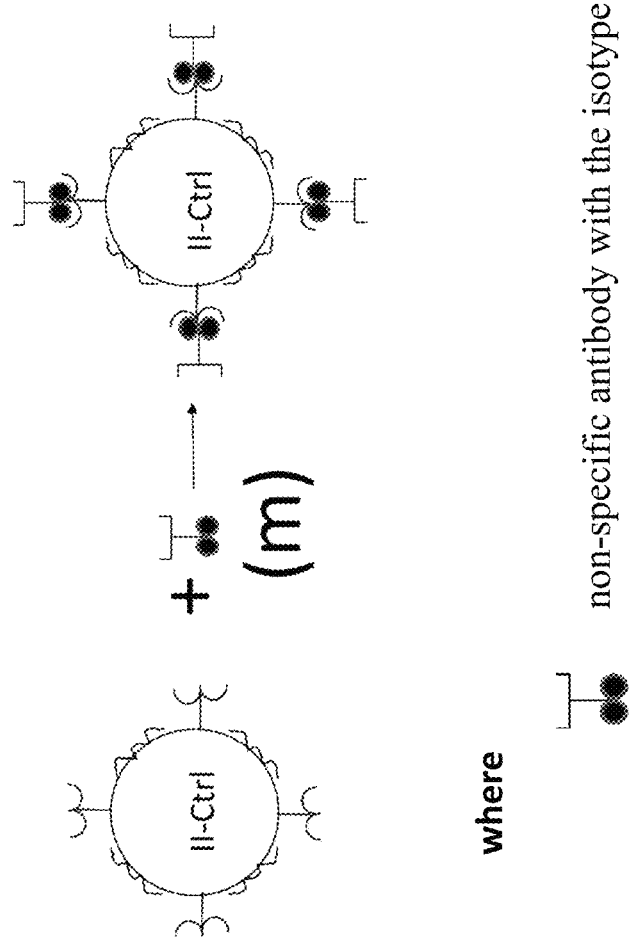

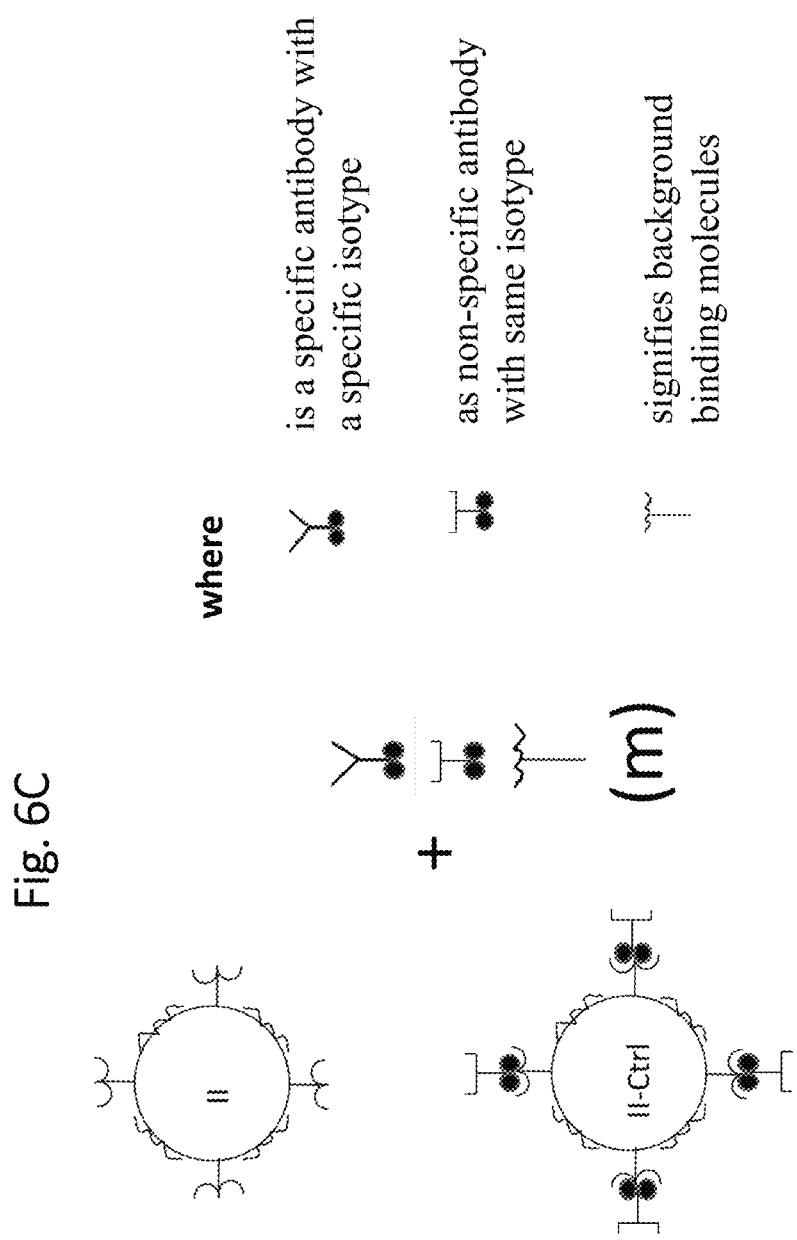

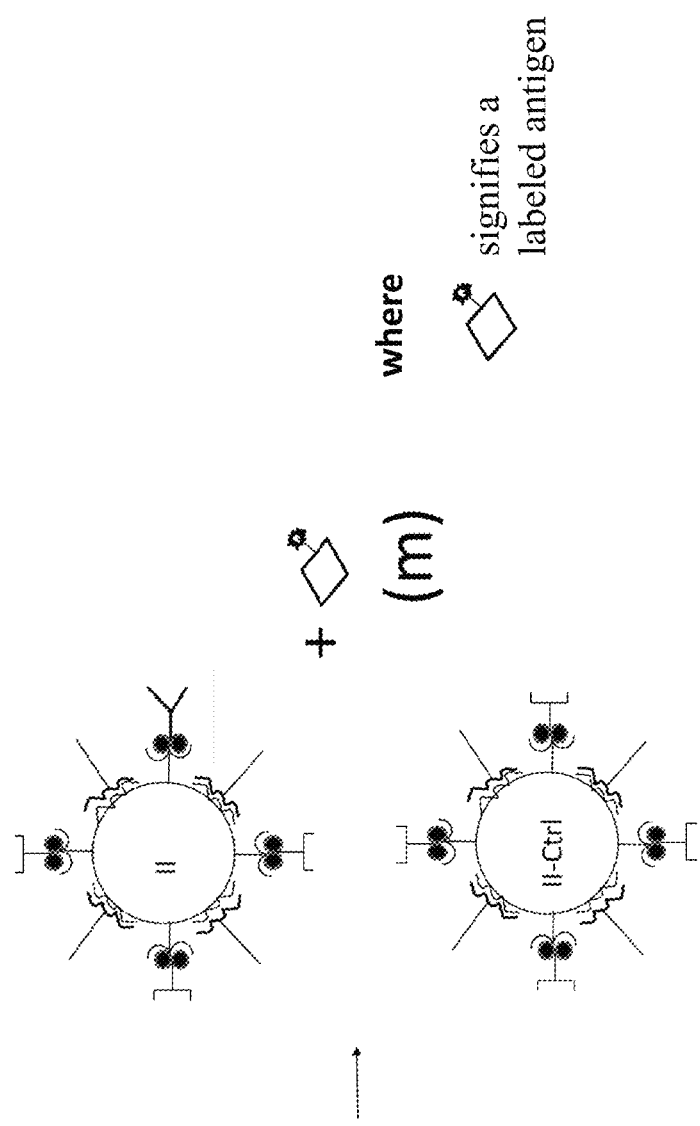

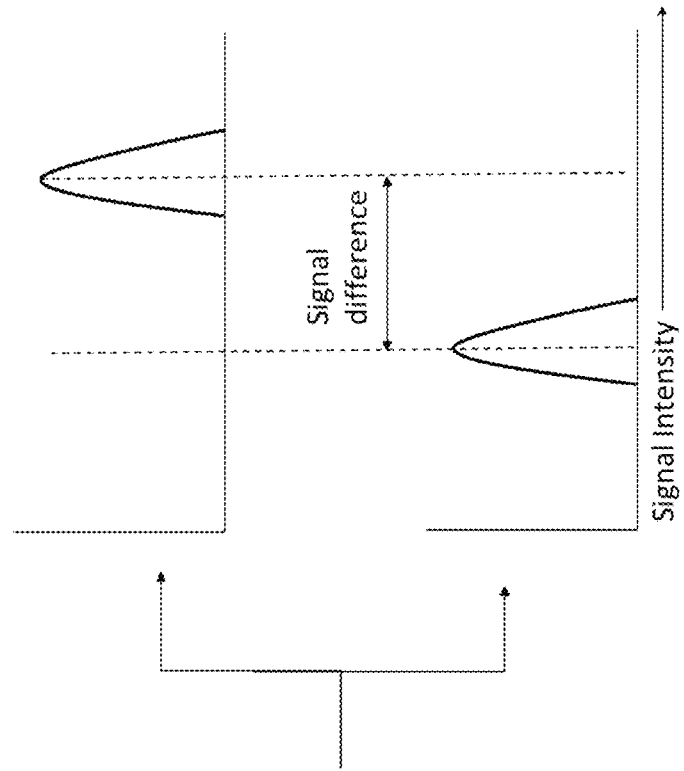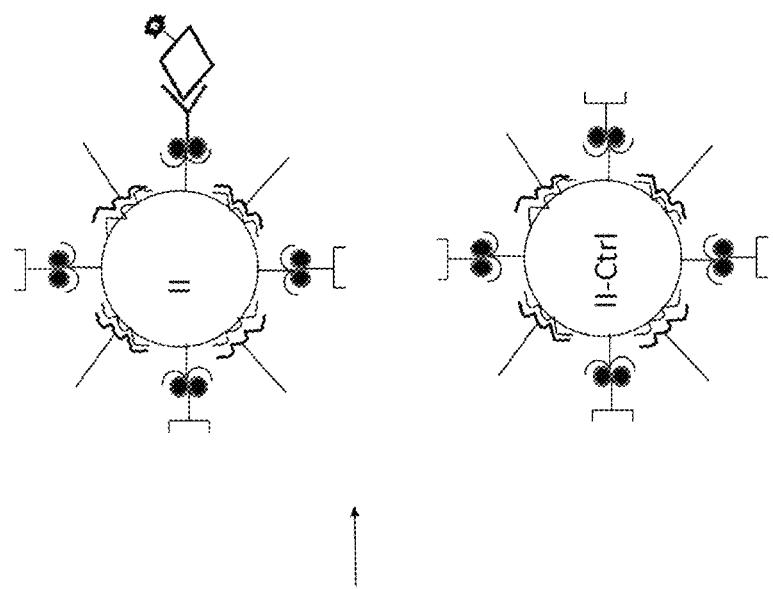

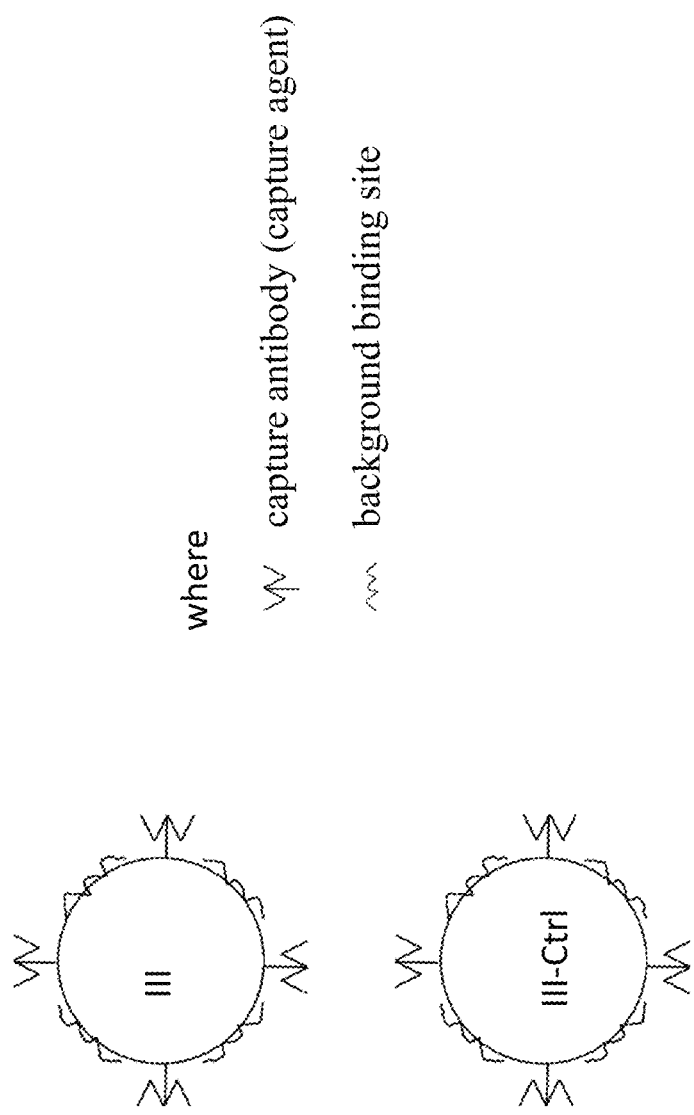

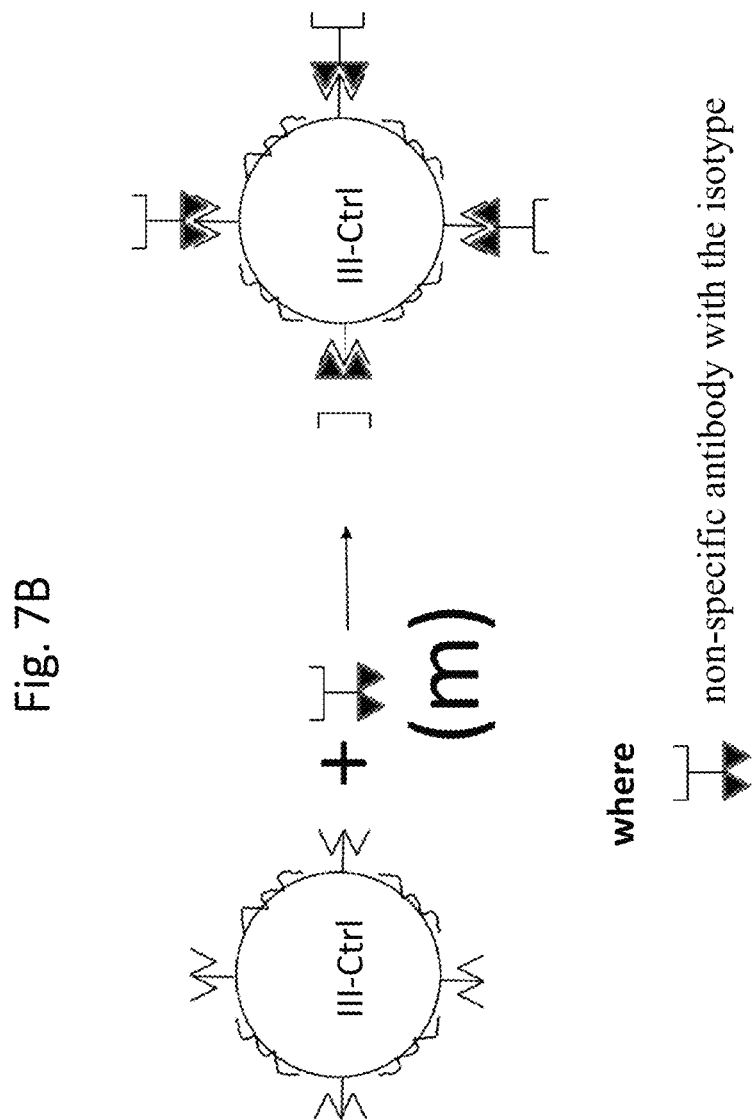

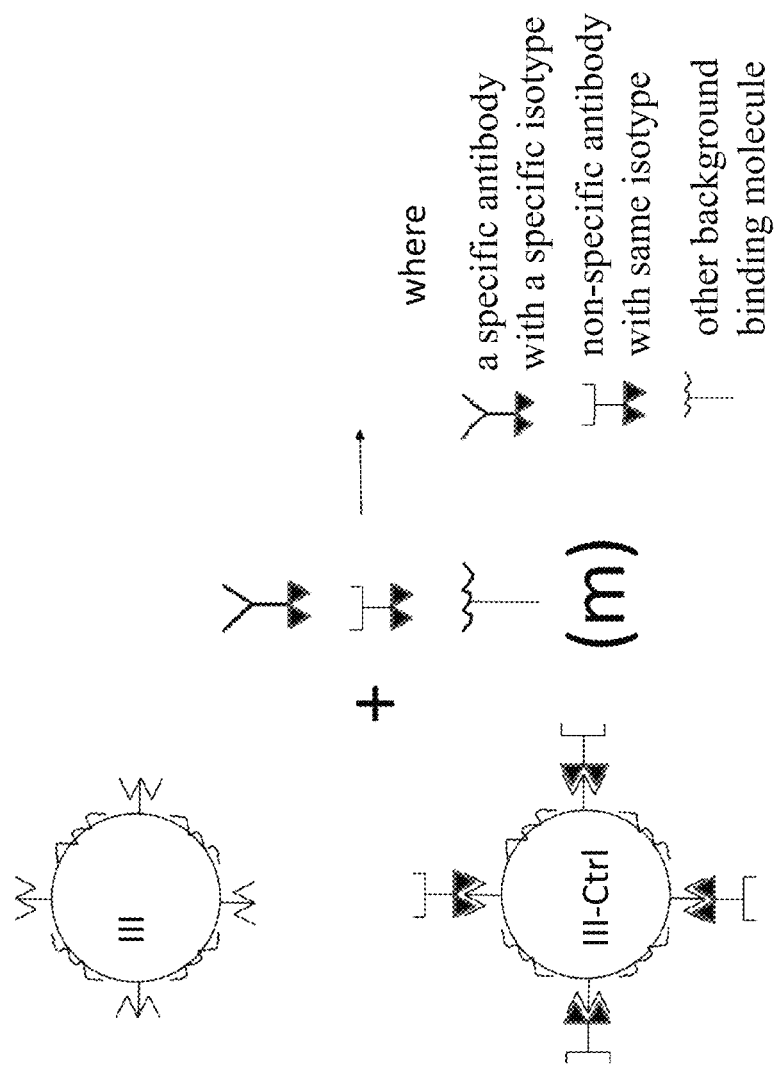

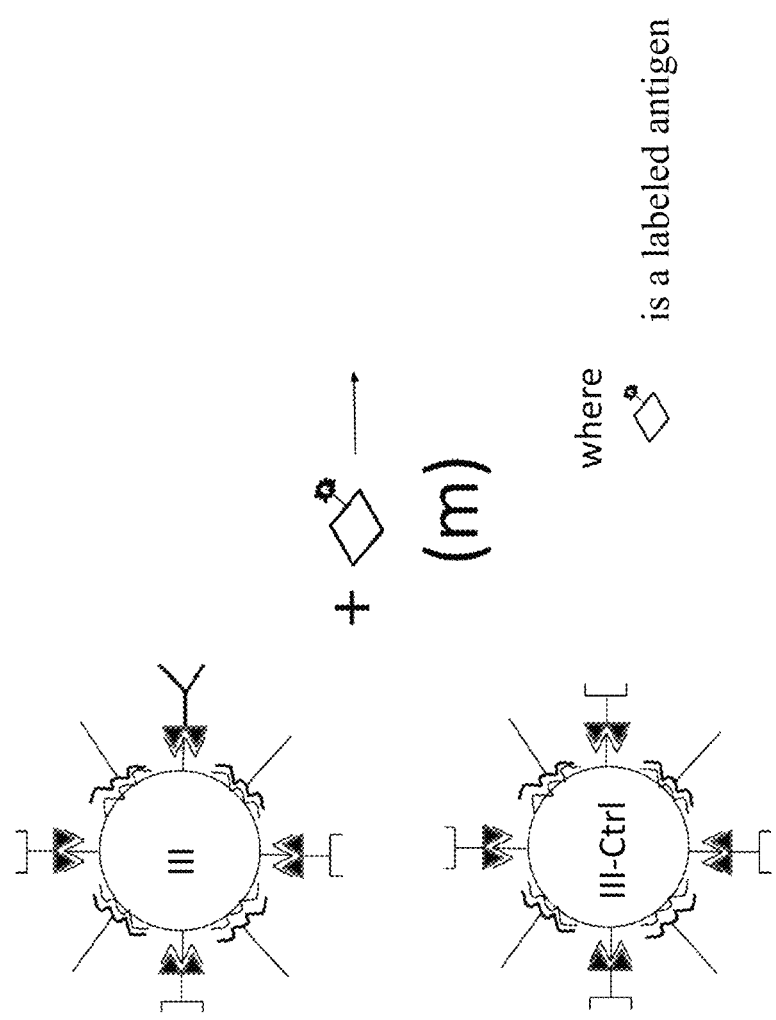

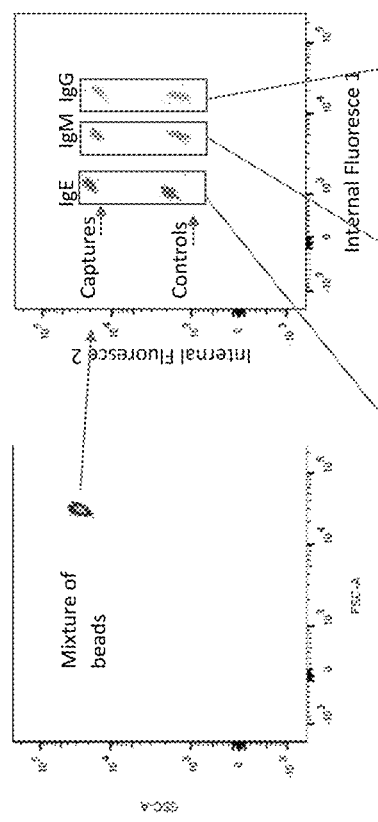
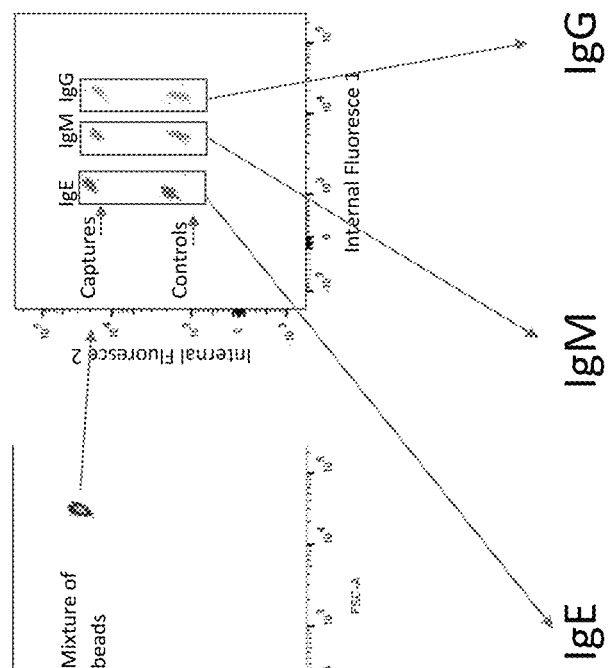
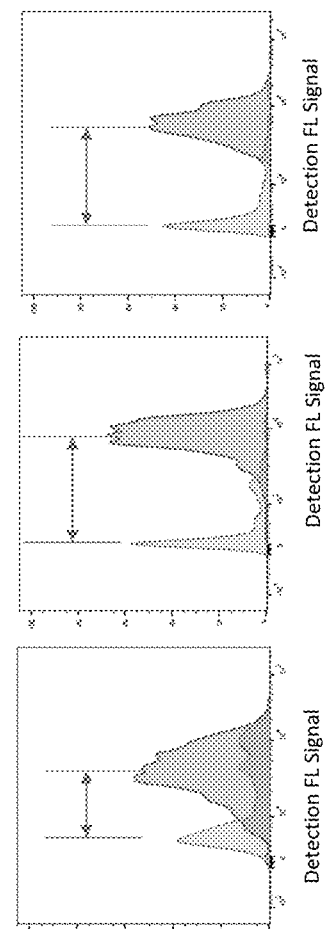
Fig. 9A
Fig. 9B
Fig. 9C

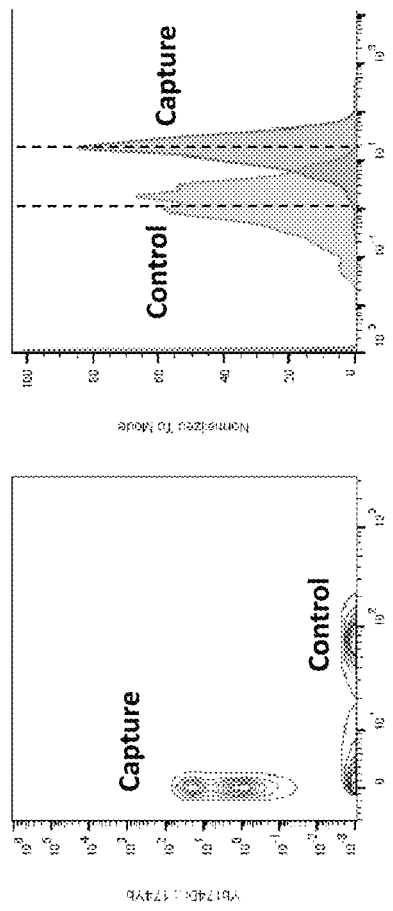
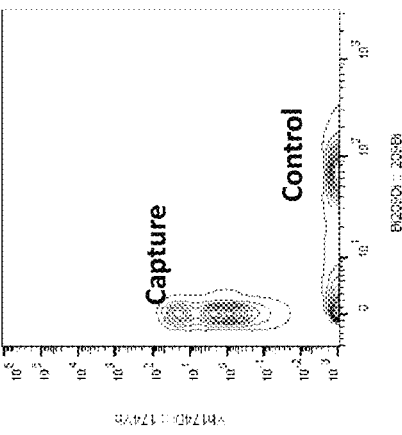
FIG. 10A / Fig. 10B / Fig. 10C / Fig. 10D

METHOD OF REMOVING NON-SPECIFIC BINDING SIGNALS USING MICROPARTICLE ASSAY

CROSS REFERENCE TO RELATED APPLICATION

This application claims priority to U.S. Provisional Application No. 62808746, filed Feb. 21, 2019, the disclosure of which is incorporate herein in its entirety.

BACKGROUND

The accurate detection and quantification of chemical and biological targets (molecules or microorganisms) in biological samples, such as blood, plasma, serum, urine, saliva and various mucosal secretion, nasopharyngeal and oropharyngeal swabs, respiratory sputum, as well as cell and tissue lysates is important for rapid and accurate diagnosis of various diseases, monitoring of disease conditions, monitoring of medical treatments, and the determination of proper treatment regimens. In many cases, the targets being detected or quantified are present in a biological sample in small amounts and are often mixed with vastly larger amounts of irrelevant or interfering components. The accurate detection of such targets or analytes requires highly sensitive and specific test methods, such as ligand binding assays.

Sensitivity and specificity are the two key elements of the diagnostic power of any ligand based binding assays. "Analytical sensitivity" represents the smallest amount of analytes in a sample that can accurately be measured by an assay. "Analytical specificity" refers to the ability of an assay to measure one particular analyte, rather than others, in a sample. In theory, sensitivity and specificity are statistical measures of the performance of a binary classification test, also known in statistics as classification function: Sensitivity (also called the true positive rate, the recall, or probability of detection in some fields) measures the proportion of positives that are correctly identified as such (e.g. the percentage of sick people who are correctly identified as having the condition). Specificity (also called the true negative rate) measures the proportion of negatives that are correctly identified as such (e.g. the percentage of healthy people who are correctly identified as not having the condition). Simply put, sensitivity is the proportion of true-positives which actually test positive, a sensitive test will rarely "miss" positive individuals; specificity is the proportion of true-negatives which actually test negative, a specific test will not produce false positives. An analytical method may fail to accurately detect analytes due to the lack of sensitivity and/or specificity. On the one hand a specific method may lack sensitivity enough to detect low amount of target analytes; on the other hand, a sensitive method may lack specificity due to the background signal.

Ligand binding assay (LBA) is an analytic detection procedure, which relies on the binding of ligand molecules to receptors, antibodies or other macromolecules. A detection method is used to determine the presence and extent of the ligand-receptor complexes formed, and this is usually determined electrochemically or through a fluorescence detection method. This type of analytic test can be used to test for the presence of target molecules in a sample that is known to bind to the receptor. Typical ligand binding assays anchor one binding partner on a solid surface therefore called Solid Phase Ligand Binding Assays, including multi-well plate assays (e.g., ELISA), On-Bead Ligand Binding assays, On-Column Ligand Binding Assay, Filter Assays, surface plasmon resonance (Biacore) and equilibrium-based methods. Although Ligand binding assays are highly specific, a variety of factors, including antibody avidity, valence of interactants, assay format, assay procedure variability, and matrix effects often limit the sensitivity and specificity of a particular method.

Biological samples for example sera, contain background binding components including natural antibodies, rheumatoid factors, and many other matrix factors that prevent the accurate analysis of the analytes in the samples. The background binding factors in test samples may complicate the detection and quantification of target analytes in the samples.

Background signals compromise both sensitivity and specificity of an assay because they cause false positive or false negative results depending on how the assay cut point sets. As illustrated in FIG. 1, when the detection signal from the analyte is much higher than the background signal, the set of cut points only affect the quantification but not the detection as positive of the target (FIG. 1C). However, when the target signal is low, the different sets of cut point result in the analyte signal be deemed as either negative or positive, totally opposite results (FIG. 1A and FIG. 1B). This uncertainty of cut point setting interferes the accurate diagnosis of life-threatening diseases, e.g., biomarkers in the early stage of disease, low level of infectious species, and low level of specific IgE for an allergen etc.

Background binding has many causes, including any factors in the test sample or in detection solution that bind with the matrix and lead to labeled detection agent bind to the matrix other than the intended target. The binding can be to the surface sites of the receptacle or to capture agent portions not covered by the intended target or unintended detection agent binding to any part of the binding chain complex.

Almost any solid-phase based assay can be affected by the matrix binding effect, including ELISA and bead-based assays. Components in the matrix other than the analytes can interact with a solid surface and interfere with the assay results. For example, if large quantities of analyte related material (e.g., natural antibodies, IgGs) are present in the test sample, the material can non-specifically bind with a solid surface in a dose-dependent manner and can be detected if anti-Ig detection agents of analytes are used in the test format. Serum/plasma components may influence assay results and it is usually necessary to dilute patient samples for testing to minimize such effects.

Assay variability comes from system variability including physically separated receptacles, complex assay procedures as well as sample variability including sample matrix and analytes concentration.

In a typical assay procedure, variability can come from any step from sample handling, sample dilution, temperature, pipetting, the sequence of reagent addition, incubation time, washing cycles. All these factors add uncertainty to assay results.

Another factor contributing to non-specific binding is the non-specific binding of analytes with the solid surface, i.e., not to specific analyte capture molecules, but directly to the surface sites, leading to the dose-dependent non-specific signal.

The complexity of the cause of background binding makes it difficult to simply deduct or remove background signal based upon normal/negative controls because each sample has its unique background components.

There are two common strategies to overcome background signals for ligand binding assays: 1) reducing background binding and 2) establishing assay cut point based upon "negative" controls. These two strategies can affect the analytical sensitivity and specificity at different directions.

ELISA has been used to detect analytes in biological samples with blank controls and/or irrelevant targets as a control on wells of the same plates with the test samples to determine plate-specific cut point (system cut point). Because limited reading range of OD and physical limitation, ELISA methods have all the potential matrix binding effect, therefore an ELISA assay often require samples to be diluted to certain degree, not only to dilute the background binding but also to dilute the analytes to the narrow window of detection range. This decreases assay sensitivity. Prior art with multiplex bead assays can simultaneously detect many attributes from one or several samples. Because the detection agent is a fluorescence-labeled reagent, the detection range is very broad. This directly leads to a broad detection range and in many screening designs, hence there is no need of dilution of samples. However, the bead-based assay has the same issue of background binding as in the ELISA assays. There are reports of background signals in commercial kits because strong signals were found on negative control beads. Efforts have been made to block these signals including pre-adsorption of rheumatoid factors from the samples or special treatment of beads. These methods were often expensive and could not fully remove the background signals on the negative control beads.

To reduce the background binding in the biological assays, such as ELISA, Western blot, micro bead-based assay, or other solid phase-based assay includes micro-chip and immunoCap, by blocking with non-specific binding materials such as BSA to "pre-occupy" those potential binding sites on the solid phase, can greatly reduce the non-specific binding of detection agents in an assay. Sometimes pre-adsorb (deplete) interfering factors from the matrix, e.g., using protein A/G pre-treatment to reduce IgG level in test serum can help to detect specific IgM and IgE antibodies. However, such non-specific blocking materials often are not able to fully block the non-specific binding sites and as such the percent of BSA in a typical binding buffer differs from 0.1% up to 10%, in the latter case it is arguable that this might block/interfere the intended specific binding of the detecting analytes with the ligand anchored on the solid phase such as the surface of ELISA plate or microbeads. In other cases, a detection agent might even react with BSA. In samples of plasma and serum, the background binding is associated with the amount of the background binding factors in the samples, as such in a typical ELISA assay, the sample needs to be diluted at least 50 fold to reduce the effect of high concentration of background binding factors, such as rheumatoid factors, natural antibodies, etc.

Another approach in practice to reduce backgrounding binding is washing with a detergent such as nonionic detergent Tween 20. While this approach removes low-affinity background binding signal, the target analyte signal is also reduced, therefore assay sensitivity is also reduced.

Many times the practice to lower background signal by dilution is a double-edged sword. When the targeted specific signal is high, a titration or dilution of test samples is necessary in order to optimize the assay signal to background signal (increase signal/noise ratio). However, when analytes concentration is low, dilution on one hand decreases background signal (i.e., decrease non-specific signal, in other words increases specificity), on the other hand, dilution of the sample will lead to dilution of analytes signal and decrease sensitivity. The relative analyte signal to background signal (noise) matters, while the background signal level is used to set as the cut point.

For a particular assay, it is relatively easy to control the system cut point. For example, plate-specific cut point in ELISA assay can demonstrate precision and consistency for quality-assured plates and detection agents. It is however extremely difficult to control sample variability as each sample has its independent background or matrix, or other independent variable. Even the same sample with different dilutions has an independent variable of background for each dilution. For serum samples, often the cut point is set based upon pooled sera or average (or range) of a certain number of "negative" samples. This cut point may be higher or lower than the actual background signal of a particular sample. Incorrect choice of the cut point would lead to false interpretation of marginal signal of the assay.

When the actual background signal or matrix binding signal is higher than the cut point generated by negative control, false positive may result. In some circumstances, the signal can even be blocked in inhibition assay (often used as specificity test) by free analytes if there is an interaction.

When an individual has a lower background than the cut-point generated by negative controls, and especially when the analyte tested in the individual has a low concentration and the binding signal is only marginal and weaker than limit of detection (LOD) established by positive control diluted in the negative sample matrix with a high background signal, it will lead to a false negative result.

Different samples have different matrixes and different background as well as different amounts of test/target analytes, all of which contributing to signal variability of a test. Even negative samples have its own matrix and background therefore, the basis of cut-point based upon negative control might have a wrong fundamental hypothesis, especially when there exist sample outliers. Different test samples, e.g., serum from two different individuals, usually have different background level for natural antibodies, rheumatoid factors. Even samples from the same individual with different disease states, or same sample with different dilution, the background levels are different. Therefore, an arbitrary cut point of LOD based upon the average of a certain number of external "normal" or negative individuals while ignoring the outliers are not necessarily the best estimation of LOD. The practice will result in some of the low marginal but true positive signals being interpreted as pseudo-positive or buried within the standard deviation range of cut-point reading.

SUMMARY OF THE INVENTION

The present disclosure provides methods and kits for accurately detecting one or more analytes in a sample by removing non-specific binding signals utilizing capture microparticles and control microparticles. These methods and kits enable much improved level of sensitivity, specificity and accuracy of current bead-based multiplex immunoassays.

In one aspect of the disclosed subject matter, a method for detecting N target analytes which are possibly present in a sample (N being a natural number equal to or greater than 1) is provided. The method comprises:

(a) to the biological sample, for each analyte of the N target analytes: adding a plurality pairs of microparticles, each pair comprising (1) a capture microparticle and (2) a corresponding control microparticle, to thereby form a mixture; wherein the capture microparticles each comprise a first substrate and at least one capture agent coupled thereon, the capture agent being active and capable of specifically binding to the analyte; wherein the control microparticles each comprise a second substrate that is not coupled with an active capture agent capable of specifically binding to the analyte;

(b) to the mixture, for each analyte of the N target analytes, adding a detection agent capable of binding to the analyte;

(c) aligning and passing each of the microparticles for each of the N target analytes in a single file in a flow cytometer while detecting (1) detection signals generated by the detection agent bound with the microparticle, and (2) the internal reference signals emitted by the substrate in the microparticle; wherein the internal reference signals of the capture microparticles and of the corresponding control microparticles are different from each other, and are each different from the detection signals;

(d) for each of the N target analytes, distinguishing the detection signals from the capture microparticles and detection signals from corresponding control microparticles based on the different internal reference signals detected;

(e) for each of the N target analytes, obtaining a first weighted value from the obtained detection signals of the capture microparticles and a second weighted value from the obtained detection signals from the corresponding control microparticles, and subtracting the second weighted value from the first weighted value to obtain a calibrated weighted value; and (f) for each analyte of the N target analytes, determining the presence or absence of the analyte in the sample based on the calibrated weighted value.

In some embodiments of the methods, the detection agent comprises a fluorescent dye, and detecting the detection signals generated by the detection agent bound with each microparticle comprises detecting fluorescence signals emitted from the microparticle.

In some embodiments, the substrate of each of the microparticles comprises a fluorescent dye, and detecting the internal reference signals emitted by the substrate in each microparticle comprises detecting fluorescence signals emitted from the microparticle. In some embodiments of the methods, the detection agent comprises a chemiluminescent dye, and detecting the detection signals generated by the detection agent bound with each microparticle comprises detecting chemiluminescent signals emitted from the microparticle.

In some embodiments of the methods, the detection agent comprises a radioactive substance, and detecting the detection signals generated by the detection agent bound with each microparticle comprises detecting radioactive signals emitted from the microparticle.

In some embodiments, the detection agent comprises a heavy metal ion tag, and detecting the detection signals generated by the detection agent bound with each microparticle comprises detecting a signal representing the heavy metal ion tag included in the detection agent in a mass spectrometer. In certain embodiments, the substrate of each of the microparticles for each analyte of the N target analytes comprises a heavy metal ion tag, wherein the heavy metal ion tag in each pair of the microparticles for any analyte of the N target analytes are different from each other and each different from the heavy metal ion tag of the detection agent, and detecting the internal reference signals emitted by the substrate in each microparticle comprises detecting a signal representing the heavy metal ion tag included in the substrate in the mass spectrometer.

In some embodiments, each of the N target analytes comprise an antibody or biotinylated antibody specific to an antigen or allergen. The antigen or allergen can be selected from the group consisting of a protein, a bacterium, a virus, a component of bacteria, a component of virus, a toxin, a drug, a drug excipient, pollen, grass, dust and peanut.

In some embodiments, each of the N target analytes can be independently selected from the group consisting of a pharmaceutical compound, a factor in blood, a protein, a bacterium, a bacteria component, a virus, a virus component, a peptide, an antibody, a toxin, a hormone, a cytokine, an immunoglobulin, an immunoglobulin Fab, a polynucleotide, a drug, a drug carrier, and a drug excipient.

In some embodiments, the sample comprises a bodily fluid (or biofluid), which can be selected from the group consisting of blood, plasma, serum, urine, saliva, mucosal secretions, nasopharyngeal and oropharyngeal swabs, respiratory sputum, snivel tears and tissue lysate. The bodily fluid can be obtained from an individual who has been diagnosed with a predetermined disease or condition, e.g., cancer.

In some embodiments, the capture agent comprises an antigen or antibody. The antigen can be selected from the group consisting of a protein, a peptide, a bacterium, a virus, a component of bacteria, a component of virus, a toxin, a hormone, a cytokine, a pharmaceutical compound, a blood factor, an immunoglobulin, an immunoglobulin Fab, a polynucleotide, a drug carrier or excipient.

In some embodiments, determining the abundance of the analyte comprises detecting the presence or absence of the analyte without quantifying the amounts of the analyte in the sample. In other embodiments, if it is determined that a certain analyte is present in the sample, the amounts of the analyte in the sample is also determined.

In some embodiments, the sample is a biological sample obtained from a human individual, a first analyte of the N target analytes is a human antibody having a known isotype and specific to a known antigen, the capture agent of each pair of microparticles and control microparticles for the first analyte comprises a capture antibody capable of binding specifically to the Fc portion of the known human antibody isotype or coupling with a receptor of Fc portion of the known human antibody isotype. The control microparticles for the first analyte includes a saturating amount of a blocking antibody binding to the amount of the capture antibody available in the control microparticles. The blocking antibody has the same known isotype, is non-specific to the known antigen or is specific to an antigen that is treatment-naïve to the individual of whom the biological sample is obtained from. The detection agent for the first analyte comprises the known antigen. In some embodiments, the known antigen is selected from a drug or a component of a natural allergen. In some embodiments, the capture antibody is a monoclonal or polyclonal anti-Fc antibody. In some embodiments, the anti-Fc antibody is an antibody specifically binds to IgG, IgA, IgM, or IgE. In some embodiments, the receptor of Fc portion is Fc-mu receptors (FcµR), Fc-gamma receptors (FcγR), Fc-alpha receptors (FcαR), Fc-alpha/mu receptor (Fcα/µR), Fc-epsilon receptors (FcεR), or FcRn.

In some embodiments, the determination of abundance of any of the N analytes in a sample comprises: for each analyte of the N target analytes: using a plurality of standard samples of varying known concentrations of the analyte which are mixed with the same pair of microparticles in (a) and with the same amounts for the same analyte and processed with the steps b)-e) to generate a series of calibrated weighted values corresponding to the varying known concentrations; obtaining a mathematical relationship between the calibrated weighted values and known concentrations of the analyte in the plurality of standard samples; and determining the abundance of the analyte in the sample based on the obtained calibrated weighted value of the analyte and the mathematical relationship. In other embodiments, the determination comprises relating (1) the calculated calibrated value for the analyte in the test sample to (2) the mathematical relationship established above between the calibrated weighted values and known concentrations of the analyte in the plurality of standard samples.

In some embodiments, when N is greater than 1, the detection agent for one analyte of the N target analytes is different from the detection agent for another analyte of the N target analytes. In other embodiments, the detection agent for each of the N target analytes are the same.

In some embodiments, when N is greater than 1, the first substrate included in the capture microparticles for one analyte of the N target analytes emits different internal reference signals than the first substrate included in the capture microparticles for another analyte of the N target analytes.

In some embodiments, when N is greater than 1, the second substrate included in the control microparticles for one analyte of the N target analytes emits different internal reference signals than the second substrate included in the control microparticles for another analyte of the N target analytes.

In another aspect, the present disclosure provides a kit for detecting one or more analytes in a sample. The kit can include: a plurality pairs of microparticles, each pair comprising (1) a capture microparticle and (2) a corresponding control microparticle, wherein the capture microparticles each comprise a first substrate and at least one capture agent coupled thereon, the capture agent being active and capable of specifically binding to an analyte possibly present in the sample; wherein the control microparticles each comprise a second substrate that is not coupled with an active capture agent capable of specifically binding to the analyte; and a detection agent capable of binding to the analyte.

In some embodiments of the kit, the detection agent comprises a fluorescent dye. In some embodiments of the kit, the detection agent comprises a chemiluminescent dye. In some embodiments of the kit, the detection agent comprises a radioactive substance. In some embodiments of the kit, the detection agent comprises a heavy metal ion tag.

In some embodiments, the first substrate and the second substrate each comprise a fluorescent dye that is different from each other and different from the fluorescent dye in the detection agent.

In some embodiments, the first substrate and the second substrate each comprise a heavy metal ion tag that is different from each other and different from the metal ion tag in the detection agent.

In some embodiments, the kit can be used to detect a specific virus or its antibodies, such as 2019-nCoV. In such embodiments, the capture nanoparticles can comprise specific virus antibodies or antigens; the corresponding control nanoparticles can comprise vehicle system only, with no virus antibodies nor virus antigens.

In some embodiments, the kit can be used to detect specific antibody (e.g., IgE) to polyethylene glycol. In such embodiments, the capture nanoparticles can comprise polyethylene glycol; the corresponding control nanoparticles can comprise vehicle system without polyethylene glycol.

BRIEF DESCRIPTION OF THE DRAWINGS

FIG. 1A shows detection signal of a sample higher than background signal BS1 (which is also chosen as cut point), therefore deemed as positive. FIG. 1B shows detection signal of the same samples deemed as negative if a different cut point BS2 is chosen. However, only one of BS1 and BS2 can be accurate. If BS1 is accurate, FIG. 1B shows a false-negative result; if BS2 is accurate, FIG. 1A shows a false-positive result. A broad range of cut point determined based upon a group of "negative" samples, will lead to sample signal between the up- and low-line, as false-negative, therefore reduce the sensitivity of an assay. FIG. 1C shows the test signal of a sample is much higher than both BS1 and BS2, therefore the result is deemed as positive no matter which cut point is chosen. In FIG. 1C case, the cut point will affect analyte quantification but not whether the test result is positive or negative.

FIGS. 2A-2H illustrates a pair of capture microparticle (carrying a capture molecule) and a corresponding control microparticle (not carrying capture molecules); both microparticles have same background binding sites for non-specific binding, in which:

FIG. 2A illustrates a capture molecule can bind specifically to an analyte;

FIG. 2B illustrates background binding sites and a background molecule can bind "non-specifically";

FIG. 2C illustrates the analyte has a binding site by the detection molecule;

FIG. 2D illustrates the background binding molecule can bind to a detection molecule;

FIG. 2E illustrates a capture microparticle having capture molecules and background binding sites, and a corresponding control microparticle that only has background binding sites. They are added into samples containing analytes as well as background-binding molecules (m means many such molecules, same for the rest of the figures);

FIG. 2F illustrates the capture molecule and the analyte form binding complex on the capture microparticle surface while background-binding molecule form binding complex with background sites on both capture microparticle and control microparticle. A detection agent is added;

FIG. 2G illustrates capture molecule-analyte-detection agent complex on the capture microparticle as well as background binding site-background binding molecule-detection agent complex on both the capture microparticle and the control microparticle;

FIG. 2H illustrates a signal intensity plot (histogram) of the detection signals from the detection molecules (by e.g. fluorescence intensity or tagged metal intensity by mass spectrometry), where the signal difference between the capture microparticle and the corresponding control microparticle is determined.

FIGS. 3A-3K illustrate a capture microparticle and a corresponding control microparticle each carrying an antibody which could specifically bind with a capture molecule (which in turn can bind specifically with an analyte), where the capture microparticle are saturated with the capture molecule to allow binding between them whereas the control microparticles are not, such that when the microparticles are both introduced to a sample having the analyte, only the capture microparticle will specifically bind with the analyte (through the capture molecule) whereas both the capture and control microparticles would bind background molecules, in which:

FIG. 3A illustrates a capture molecule (capture agent) specifically binds to a capture antibody;

FIG. 3B illustrates a capture molecule specifically bind to an analyte (an antibody);

FIG. 3C illustrates a background binding structure binds to a background-binding molecule;

FIG. 3D illustrates that the analyte binds to a labeled detection agent;

FIG. 3E illustrates that the background binding molecule binds with the labeled detection agent;

FIG. 3F illustrates a capture microparticle carrying capture antibodies specifically binding with capture molecules; FIG. 3G illustrates that a control microparticle is incubated in a buffer, therefore does not bind with capture molecules; (Note although only one capture microparticle and one corresponding control microparticle are shown in FIG. 3F and FIG. 3G (together they constitute a pair of microparticles), it is understood that in a test or experiment there can be hundreds, thousands, millions or more of such pairs used)

FIG. 3H illustrates that microparticles shown in 3F and 3G are incubated with a sample containing analytes and background-binding molecules;

FIG. 3I illustrates the capture microparticle with capture antibody-capture molecule-analyte complex as well as background structure-background binding molecules complex, and the corresponding control microparticle with only background structure-background binding molecules complex. When incubated with the labeled detection agent, the capture microparticle and the control microparticle form complex as illustrated in FIG. 3J.

FIG. 3J illustrates the capture microparticle with the detection agent bound with analytes as well as with background-binding molecules, and the control microparticle with detection agent bound with background-binding molecules.

FIG. 3K is a signal intensity plot (histogram) of the detection signals from the detection molecules (by e.g. fluorescence intensity or tagged metal intensity by mass spectrometry), the signal difference between the capture microparticle and the corresponding control microparticle is determined.

FIGS. 4A-4H illustrate a capture microparticle carrying polyethylene glycol (PEG) and corresponding control microparticle not carrying PEG after co-incubation with a serum sample taken from a mouse immunized with polyethylene glycol, both showed a titration-dependent binding signal of PE-labeled anti-mouse Igs. Control microparticle signal is associated with the background binding while the capture microparticle signal is associated with both specific binding of anti-PEG Igs and background binding.

FIG. 4A illustrates FSC (forward scatter light) and SSC (side scatter light) parameters of microparticles from the fluorescence flow cytometry (FFC) showing that the signals from capture microparticles and control microparticles are indistinguishable;

FIG. 4B illustrates fluorescence signals of capture microparticles and control microparticles separated by internal fluorescence of the substrate of the microparticles (different polystyrene beads);

FIG. 4C shows a histogram of detection signals from capture microparticles at one serum titration;

FIG. 4D shows a histogram of detection signals from corresponding control microparticles at the same titration as FIG. 4C;

FIG. 4E depicts histograms from FIG. 4A and FIG. 4B arranged side-by-side, showing the signal difference;

FIG. 4F and FIG. 4G are plots of weighted fluorescence intensity of the capture microparticles and that of the corresponding control microparticles against serum titration factor;

FIG. 4H is a plot of the difference of weighted fluorescence intensity of the capture microparticles and that of the corresponding control microparticles against serum titration factor.

FIGS. 5A-5F illustrates a work flow of obtaining calibrated signals for a first analyte in a sample using a first series of capture microparticles referred to as I and corresponding control microparticles referred to as I-Ctrl. Although only one capture microparticle and one corresponding control microparticle are shown (together they constitute a pair of microparticles), it is understood that in a test or experiment there can be hundreds, thousands, millions or more of such pairs used. Both the capture microparticles and the control microparticles for this series carry a same capture antibody (a specific anti-isotype antibody) and have the same background binding feature, but I-Ctrl has been pre-occupied with an irrelevant antibody with the same isotype as the first analyte, which is an isotype antibody in the sample that can specifically bind with a known antigen (a drug or an allergen). The antigen includes a signaling portion and is herein considered a detection agent.

FIG. 5A illustrates a capture microparticle (I) and its corresponding control microparticle (I-Ctrl) both carrying a same capture antibody, a specific anti-isotype antibody, both microparticles having the same background binding feature;

FIG. 5B schematically shows the I-Ctrl control microparticle is pre-occupied and saturated with an isotype control antibody with its isotype specifically bound by the capture antibody (in this manner, the I-Ctrl microparticle is inactivated and is therefore not capable of binding to the analyte specifically);

FIG. 5C schematically shows the capture microparticle I and control microparticle I-Ctrl which has been saturated with the isotype antibody are both incubated with a sample containing a first analyte (a specific antibody with a first specific isotype), non-specific antibodies with the same isotype as the first analyte and other background binding molecules;

FIG. 5D schematically shows the capture microparticle I bound by the first analyte and I-Ctrl microparticle not bound by the first analyte are both incubated with an antigen having a signaling portion (e.g., a detection agent) and capable of specially binding to the first analyte;

FIG. 5E schematically shows the capture microparticle I bound by the first analyte, specifically bind with the labeled antigen while the control microparticle I-Ctrl does not bind with the labeled antigen. Other than the labeled antigen, both microparticles bear the same background binding sites and therefore bind the same background-binding molecules from the sample;

FIG. 5F schematically shows detection signal intensity histograms (generated by the labeled antigen, e.g., from fluorescence intensity or by mass spectrometry detection of tagged-metal intensity in a fluorescence flow cytometry or a mass cytometry). The signal difference between the capture microparticle I and the corresponding control microparticle I-Ctrl is determined.

FIGS. 6A-6F illustrates a work flow of obtaining calibrated signals for a second analyte in a sample using a second dual-series of capture microparticles referred to as II and corresponding control microparticles referred to as II-Ctrl. Although only one capture microparticle and one corresponding control microparticle are shown (together they constitute a pair of microparticles), it is understood that in a test or experiment there can be hundreds, thousands, millions or more of such pairs used. Both the capture microparticles and the control microparticles for this series carry a same capture antibody (a specific anti-isotype antibody) and have the same background binding feature, but II-Ctrl has been pre-occupied with an irrelevant antibody with the same isotype as the second analyte, which is an isotype antibody in the sample that can specifically bind with a known antigen (a drug or an allergen). Shown here the antigen (or detection agent) can be the same as the antigen in FIG. 5A.

FIG. 6A illustrates a capture microparticle (II) and its corresponding control microparticle (II-Ctrl) both carrying a same capture antibody, a specific anti-isotype antibody, both microparticles having the same background binding feature;

FIG. 6B schematically shows the II-Ctrl control microparticle is pre-occupied and saturated with an isotype control antibody with its isotype specifically bound by the capture antibody (in this manner, the II-Ctrl microparticle is inactivated and is therefore not capable of binding to the analyte specifically);

FIG. 6C schematically shows the capture microparticle II and control microparticle II-Ctrl which has been saturated with the isotype antibody are both incubated with a sample containing a second analyte (a specific antibody with a second specific isotype), non-specific antibodies with the same isotype as the second analyte and other background binding molecules;

FIG. 6D schematically shows the capture microparticle II bound by the second analyte and II-Ctrl microparticle not bound by the second analyte are both incubated with an antigen having a signaling portion (e.g., a detection agent) and capable of specially binding to the second analyte;

FIG. 6E schematically shows the capture microparticle II bound by the second analyte, specifically bind with the labeled antigen while the control microparticle II-Ctrl does not specifically bind with the labeled antigen. Other than the labeled antigen, both microparticles bear the same background binding sites and therefore bind the same background-binding molecules from the sample;

FIG. 6F schematically shows detection signal intensity histograms (generated by the labeled antigen, similar to that of FIG. 5F). The signal difference between the capture microparticle II and the corresponding control microparticle II-Ctrl is determined.

FIGS. 7A-7F illustrates a work flow of obtaining calibrated signals for a third analyte in a sample using a third dual-series of capture microparticles referred to as III and corresponding control microparticles referred to as III-Ctrl. Although only one capture microparticle and one corresponding control microparticle are shown (together they constitute a pair of microparticles), it is understood that in a test or experiment there can be hundreds, thousands, millions or more of such pairs used. Both the capture microparticles and the control microparticles for this series carry a same capture antibody (a specific anti-isotype antibody) and have the same background binding feature, but III-Ctrl has been pre-occupied with an irrelevant antibody with the same isotype as the third analyte, which is an isotype antibody in the sample that can specifically bind with a known antigen (a drug or an allergen). Shown here the antigen (or detection agent) can be the same as the antigen in FIG. 5A and/or FIG. 6A.

FIG. 7A illustrates a capture microparticle (III) and its corresponding control microparticle (III-Ctrl) both carrying a same capture antibody, a specific anti-isotype antibody, both microparticles having the same background binding feature;

FIG. 7B schematically shows the III-Ctrl control microparticle is pre-occupied and saturated with an isotype control antibody with its isotype specifically bound by the capture antibody (in this manner, the III-Ctrl microparticle is inactivated and is therefore not capable of binding to the analyte specifically);

FIG. 7C schematically shows the capture microparticle III and control microparticle III-Ctrl which has been saturated with the isotype antibody are both incubated with a sample containing a third analyte (a specific antibody with a third specific isotype), non-specific antibodies with the same isotype as the third analyte and other background binding molecules;

FIG. 7D schematically shows the capture microparticle III bound by the third analyte and III-Ctrl microparticle not bound by the third analyte are both incubated with an antigen having a signaling portion (e.g., a detection agent) and capable of specially binding to the third analyte;

FIG. 7E schematically shows the capture microparticle III bound by the third analyte, specifically bind with the labeled antigen while the control microparticle III-Ctrl does not specifically bind with the labeled antigen. Other than the labeled antigen, both microparticles bear the same background binding sites and therefore bind the same background-binding molecules from the sample;

FIG. 7F schematically shows detection signal intensity histograms (generated by the labeled antigen, similar to that of FIG. 5F and/or FIG. 6F). The signal difference between the capture microparticle III and the corresponding control microparticle III-Ctrl is determined.

FIG. 8A illustrates capture microparticles (I, II, III) and their corresponding control microparticles (I-Ctrl, II-Ctrl, and III-Ctrl), where the control microparticles are pre-occupied and saturated with isotype control antibodies, incubated with a sample containing three different analytes shown in FIGS. 5C, 6C and 7C, non-specific antibodies shown in FIGS. 5C, 6C and 7C, and other background binding molecules; FIG. 8B schematically shows the capture microparticles bound by the respective analytes and control microparticles not bound by the analytes are both incubated with antigens having a signaling portion (e.g., a detection agent) and capable of specifically binding to the analytes; FIG. 8C schematically shows the capture microparticles bound by the respective analytes specifically bind with the labeled antigens while the control microparticles do not specifically bind with the labeled antigens. FIG. 8D schematically shows detection signal intensity histograms for the capture microparticles and the corresponding control microparticles.

FIGS. 9A-9C shows three example series of pairs of human Ig capture microparticles, i.e., IgG, IgM and IgE incubated with a sample containing human anti-PEG antibodies (IgG, IgM & IgE isotypes) were able to detect the presence and distinguish isotypes of such antibodies of different isotypes. FIG. 9A shows FSC and SSC of mixture microparticles by fluorescence flow cytometry. FIG. 9B shows the three series of pairs of microparticles (total of 6 types) distinguished by internal fluorescence of the microparticles. FIG. 9C shows overlapping histograms of capture microparticles and control microparticles of each isotype pair by detection fluorescence signal (i.e., PEG-conjugated PE).

FIG. 10A-10D show metal-tagged pair of capture microparticle and control microparticle added into two human serum samples with different amount of anti-PEG IgG and with different background, were able to detect the background difference and presence of anti-PEG IgG by mass cytometry. FIG. 10A is a contour plot of internal mass spectroscopy signals to distinguish capture microparticles (containing a substrate tagged with 174Yb) and control microparticles (containing a substrate tagged with 209Bi) in a mass cytometry for a first serum sample containing standard human anti-PEG IgG. FIG. 10B is an overlap of detection signal histogram (145Nd-labeled anti-human IgG) of capture microparticle and control microparticle for the first serum sample.

FIG. 10C is a contour plot (similar to in FIG. 10A) of internal mass spectroscopy signals of capture microparticles and control microparticles in a mass cytometry for a second serum sample containing standard anti-PEG IgG. FIG. 10D is an overlap of detection signal histogram for the second serum sample of the capture microparticles and the control microparticles.

DETAILED DESCRIPTION

It has now been discovered that low amount of analytes in a sample (e.g., a biological sample) can be identified f by self-calibrated multi-step process, and the quantity of a target analyte can be determined using data generated for the multiple known concentrations of standard analyte. In some embodiments, the analyte per se is not amplified.

In one aspect of the disclosed subject matter, a method for detecting N target analytes which are possibly present in a biological sample, N being a natural number equal to or greater than 1, the method comprising:

(a) to the biological sample, for each analyte of the N target analytes: adding a plurality pairs of microparticles, each pair comprising (1) a capture microparticle and (2) a corresponding control microparticle, to thereby form a mixture; wherein the capture microparticles each comprise a first substrate and at least one capture agent coupled thereon, the capture agent being active and capable of specifically binding to the analyte; wherein the control microparticles each comprise a second substrate that are not coupled with an active capture agent capable of specifically binding to the analyte;

(b) to the mixture, for each analyte of the N target analytes, adding a detection agent capable of binding to the analyte;

(c) aligning and passing each of the microparticles for each of the N target analytes in a single file in a flow cytometer while detecting (1) detection signals generated by the detection agent bound with the microparticle, and (2) the internal reference signals emitted by the substrate in the microparticle; wherein the internal reference signals of the capture microparticles and of the corresponding control microparticles are different from each other, and are each different from the detection signals;

(d) for each of the N target analytes, distinguishing the detection signals from the capture microparticles and detection signals from corresponding control microparticles based on the different internal reference signals detected;

(e) for each of the N target analytes, obtaining a first weighted value from the obtained detection signals of the capture microparticles and a second weighted value from the obtained detection signals from the corresponding control microparticles, and subtracting the second weighted value from the first weighted value to obtain a calibrated weighted value; and (f) for each analyte of the N target analytes, determining the abundance of the analyte in the biological sample based on the calibrated weighted value.

Figure 11:
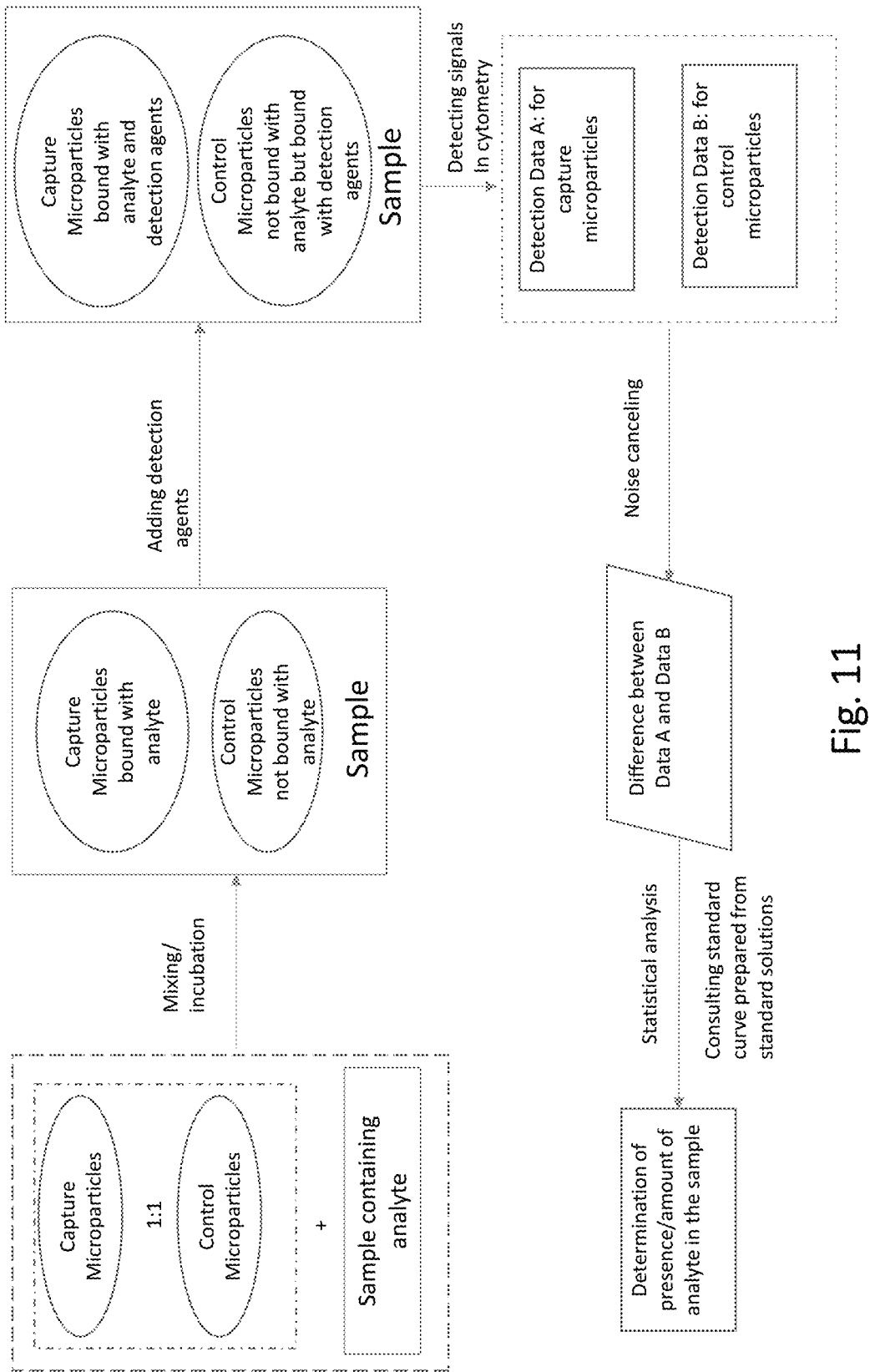
FIG. 11 depicts a general flow diagram of a method of detecting an analyte in a sample according to some embodiments of the invention.

The above workflow is schematically depicted in the flow chart shown in FIG. 11, the details of which are further described below. FIGS. 2A-2H, FIGS. 3A-3K, FIGS. 5A-5F, FIGS. 6A-6F, FIGS. 7A-7F, FIGS. 8A-8D together with associated description relate to certain embodiments of the general method.

In another aspect, the present disclosure provides kits for detecting one or more analytes in a sample, the kit comprising: a plurality pairs of microparticles, each pair comprising (1) a capture microparticle and (2) a corresponding control microparticle, wherein the capture microparticles each comprise a first substrate and at least one capture agent coupled thereon, the capture agent being active and capable of specifically binding to an analyte possibly present in the sample; wherein the control microparticles each comprise a second substrate that is not coupled with an active capture agent capable of specifically binding to the analyte; and a detection agent capable of binding to the analyte. The description hereinafter relating to the aspects of the various embodiments is pertinent to both the disclosed methods and kits.

As used herein, a microparticle is a particle which can be detected and analyzed by flow cytometry or mass cytometry. The term "microparticle" encompasses microspheres, beads, microbeads and other particles that are detectable by flow cytometry.

A microparticle can include a substrate or core and surface functional groups coupled on the substrate. The substrate can be a bead.

In some embodiments, the microparticle can have an ellipsoidal shape, e.g., spherical. In some embodiments, the microparticle can have a diameter in the range of about from 0.5 to 25 microns.

In some embodiments, the microparticle is labeled with one or more colored or fluorescent dyes. Microparticles that may be used in flow cytometry, including those labeled with a colored or fluorescent dye, are known in the art and are commercially available. Microparticle labeled with a colored or fluorescent dye can be prepared by methods including, but not limited to, methods described in U.S. Pat. Nos. 4,267,234, 4,552,812, 5,194,300, 5,073,498, 5,981,180 and 6,599,331, the teachings of which are incorporated by reference herein in their entirety.

Each subset of microparticles in a population is distinguishable from other subsets, if any others are present, based on one or more detectable parameters. In one embodiment, the detectable parameter is fluorescence intensity, size and/or shape of the microparticle.

Microparticles comprise any material or materials that can be utilized in flow cytometry. These materials include, but are not limited to, polystyrene, brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, latex, carbohydrate (e.g., carboxymethyl cellulose, hydroxyethyl cellulose), agar, gel, proteinaceous polymer, polypeptide, eukaryotic and prokaryotic cells, lipid, metal, resin, latex, rubber, silicone (e.g., polydimethyldiphenyl siloxane), glass, ceramic, charcoal, kaolinite, bentonite or combinations thereof. The microparticles may have additional surface functional groups to facilitate their attachment, adsorption and/or labeling. These groups may include, for example, carboxylates, esters, alcohols, carbamides, aldehydes, amines, sulfur oxides, nitrogen oxides, or halides. In one embodiment, the microparticles are BD™ Cytometric Bead Array (CBA). In some embodiments, the microparticles can comprise superparamagnetic, magnetic or magnetizable microparticles.

As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc domain". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The Fc domain includes portions of two heavy chains contributing to two or three classes of the antibody. The Fc domain may be produced by recombinant DNA techniques or by enzymatic (e.g. papain cleavage) or via chemical cleavage of intact antibodies.

As used herein, when a first molecule (e.g., a capture agent or molecule, such as an antibody) "specifically binds" with or "specific to" a second molecule (e.g., an analyte, or another antibody, or an antigen), it is meant that the first molecule or a portion thereof binds with the second molecule but does not substantially bind to other substances that are not the second molecule. Preferably, the first molecule and second molecule bind with "high affinity," namely with a $K_D$ of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less. As used herein, when a first molecule "does not substantially bind" to a second molecule, it is meant that the first molecule and the second molecule cannot bind or does not bind with a high affinity i.e., bind with an $K_D$ of $2\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "binding protein" includes natural protein binding domains (such as cytokine, cytokine receptors), antibody fragments (such as Fab, scFv, diabody, variable domain derived binders, VHH nanobody), alternative scaffold derived protein binding domains (such as Fn3 variants, ankyrin repeat variants, centyrin variants, avimers, affibody) or any protein recognizing specific antigens.

As used herein, the term "m" means many and in some circumstances a saturating amount of molecules or reagents indicated. The term "+" means adding two substances together. The symbol "→" means to the next step.

As used herein, the term "determining the abundance" of an analyte in a sample means determining the amounts of the analyte in the sample as well as determining a simple presence or absence of the analyte in the sample.

The term "individual," as used herein preferably refers to a human, but also encompasses other mammals. It is noted that, as used herein, the term "patient," "subject" are used as synonyms and interchangeably.

In some embodiments, the analyte(s) being detected in the sample comprise an antibody, a protein or a polypeptide. In some embodiments, the analyte(s) can be antibody or biotinylated antibody specific to an antigen or allergen, wherein the antigen can be bacteria, a component of the bacteria, a virus/a component of the virus, a toxin, pollen, grass, dust, peanut, a drug, a drug excipient, in a biological sample. In some embodiments, the analyte(s) can be a pharmaceutical compound, a factor in blood, a protein, a bacteria, a bacteria component, a virus, a virus component, a peptide, an antibody, a toxin, a hormone, a cytokine, an immunoglobulin, an immunoglobulin Fab, a polynucleotide, a drug, a drug carrier, and a drug excipient. The drug carrier is a vehicle in the process of drug delivery, and can be selected from the group of liposomes, polymeric micelles, microspheres, nanoparticles, proteins, IgG Fc, polyethylene glycol (PEG).

In some embodiments, the analyte(s) can be a component of a pathogenic organism in a sample. The component can be a protein or polypeptide. The pathogenic organism can be any pathogenic or organism including but not limited to those of bacterial, viral, fungal, mycoplasmal, rickettsial, chlamydial or protozoal origin. Some examples of pathogenic organisms include *Acintobacter, Actinomyces, Aerococcus, Aeromonas, Alclaigenes, Bacillus, Bacteriodes, Bordetella, Branhamella, Bevibacterium, Campylobacter, Candida, Capnocytophagia, Chlamydia, Chromobacterium, Clostridium, Corynebacterium, Cryptococcus, Deinococcus, Enterococcus, Erysielothrix, Escherichia, Flavobacterium, Gemella, Gonorrhea, Haemophilus, Klebsiella, Lactobacillus, Lactococcus, Legionella, Leuconostoc, Listeria, Micrococcus, Mycobacterium, Neisseria, Nocardia, Oerskovia, Paracoccus, Pediococcus, Peptostreptococcus, Propionibacterium, Proteus, Psuedomonas, Rahnella, Rhodococcus, Rhodospirillium, Staphlococcus, Streptomyces, Streptococcus, Vibrio*, and *Yersinia*. Viruses that can be detected include, but are not limited to, the hepatitis viruses and human immunodeficiency viruses (HIV). In such embodiments, the disclosed methods can further include determining the presence of a disease in the patient from whom the biological sample is obtained from, the disease being mediated by the pathogenic organism.

In some embodiments, the disclosed methods can determine the abundance of multiple different analytes simultaneously in one sample, i.e., N can be 2, 3, 4, 5, 6, 7, 8, 9, 10, 20, 30, 40, 50, 60, 70, 80, 90, 100, 200, 300, 400, 500, 1000, 2000, 5000, 10000, 100000, 1000000 or greater, or any natural numbers therebetween.

In certain embodiments, the flow cytometry used in the methods includes fluorescence flow cytometry. In other embodiments, the flow cytometry includes mass cytometry. Flow cytometric technology has been described extensively in the literature (for example, in U.S. Pat. Nos. 5,736,330, 5,981,180, 6,499,562 and 6,649,414, the teachings of which are incorporated by reference herein in their entirety). Any flow cytometer that can analyze the samples (e.g., biological samples) and/or the standard and target analytes can be utilized. Such flow cytometry technology includes, for example, Coulter Elite-ESP flow cytometer (available from Beckman-Coulter, Inc., Fullerton, Calif.), EPCS-XL MCL flow cytometer (available from Beckman Coulter, Inc.), FACScan flow cytometer (available from Beckman Coulter), MOFLO flow cytometer (available from Cytomation, Inc., Fort Collins, Colo.), Luminex 100 xMAP (available from Luminex Corp., Austin, Tex.), Luminex xMAP® technology (available from Luminex Corp.), and BD flow cytometer (e.g., BD Accuri™, BD FACSCalibur™, BD FACSCanto™, BD LSRFortessa™, BD LSRFortessa™ X-20 etc.). Mass cytometry is a fusion of two experimental platforms: flow cytometry and elemental mass spectrometry (Matthew H. Spitzer, VOLUME 165, ISSUE 4, P780-791, May 5, 2016,). Available instrumentation for mass cytometry includes but not limited to Cytometry by Time-Of-Flight (CyTOF). In certain embodiments, the methods described herein utilize a combination of mass cytometry and flow cytometry for the analysis of the analyte.

As used herein, a sample to be analyzed by the present methods for possible target analyte(s) may be any sample that comprises a polypeptide, a protein, a lipid, and/or a glucide. In one embodiment, the sample is a biological sample. Such biological samples, include, but are not limited to, samples that comprise one or more cells and samples from any organism, including, but not limited to, any animal, bacteria, plant or virus. Biological samples also include ex vivo and in vivo samples. A biological sample can, for example, include blood, synovial fluid, cerebrospinal fluid, semen and tissue samples. Tissue samples include, for example, samples from organs, tumors, lymph nodes and vascular tissue (e.g., arteries).

In some embodiments, the biological sample can be a biofluid (body fluid, or bodily fluid) sample. The biofluid sample can include but is not limited to blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, and a combination thereof. The biofluid sample may be chemically treated, e.g., biotinylated.

Many biofluids contain circulating biomacromolecules. Examples of these biofluids include blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, tissue and cell lysate, or a combination thereof. In some embodiments, the biofluid sample is obtained from a subject who has been diagnosed with cancer based on tissue or liquid biopsy and/or surgery or clinical grounds.

According to the disclosed methods, capture microparticles can include a capture agent that is active and capable of specifically binding to the target analyte. Agents that can be incorporated into the microparticles include, but are not limited to, aptamers, antibody, binding protein, allergen, drugs, oligonucleotides that are complementary to the target and/or standard nucleic acids. Oligonucleotides that are complementary to the target and/or standard nucleic acid, or a portion thereof, include nucleic acid that are complementary to sequences from naturally-occurring nucleic acids (i.e., nucleic acids that are found in an organism, for example, genomic DNA, complementary DNA (cDNA), chromosomal DNA, plasmid DNA, mRNA, tRNA, and/or rRNA). In some embodiments, the oligonucleotide that is coupled to the microparticle is a modified oligonucleotide. "Modified" oligonucleotides are oligonucleotides that comprise modified nucleotides. As used herein, a modified nucleotide is a nucleotide that has been structurally altered so that it differs from a naturally-occurring nucleotide. Such modified nucleotides include nucleotides which contain a modified sugar moiety, a modified phosphate moiety and/or a modified nucleobase. Modified nucleotides also encompass conjugated nucleotides (e.g., nucleotides conjugated to a moiety). Examples of such modified nucleotides include, but are not limited to, dideoxynucleotides, biotinylated nucleotides, amine-modified nucleotides, alkylated nucleotides, fluorophore-labeled nucleotides, radiolabeled nucleotides, phosphorothioates, phosphoramidites, phosphites, ring atom-modified derivatives and the like. Oligonucleotides can further encompass oligonucleotide polymers that possess a modified backbone, such as protein-nucleic acids (PNAs) or PNA hybrids for producing modified nucleotides and/or oligonucleotide polymers that possess a modified backbone, e.g., PNA, PNA hybrid, are well known to those of skill in the art.

In some embodiments, the capture agent is selected from the group consisting of a protein, a peptide, a bacteria, a virus, a component of bacteria, a component of virus, a toxin, a hormone, a cytokine, a pharmaceutical compound, a blood factor, an immunoglobulin, an immunoglobulin Fab, a polynucleotide, a drug carrier or excipient.

In some embodiments, the control microparticles can also include a capture agent, but such a capture agent is blocked or otherwise inactivated such that the control particles will not be able to specifically bind with the target analyte.

The capture agent can be directly coupled to the substrate of the capture microparticles by chemical bonds, or indirectly through a linker, e.g., by specific binding between the capture agent and surface functional groups immobilized on the substrate. In the latter case, for example, a capture agent (e.g., a capture antibody) can be incorporated into a microparticle for capturing analyte by specifically binding to an antibody first chemically immobilized to the substrate of the microparticle.

In the present methods, the microparticles are used in pairs, each pair including a capture microparticle and a corresponding (or associated) control microparticle, which are not physically coupled or connected in any way. In practice, when substantially the same number of capture microparticles and corresponding control particles are used together, it is considered that each microparticle has a "counterpart" in a pair. Preferably, the discrepancy between the number of the capture microparticles and the corresponding microparticles should be less than 5%, or more preferably less than 1%.

For each analyte in the sample, multiple (e.g., thousands or millions or more) identical pairs of microparticles can be used, wherein in each pair, the capture microparticle and the control microparticle are indistinguishable in their general physical properties such as base substrate material, microparticle size and microparticle surface binding sites. The capture microparticle as well as the control microparticles can have background binding sites which may bind substances in the test sample which eventually give detection signals. However, the substrate of the capture microparticle and substrate of the control microparticle may be labeled with different colored or fluorescent dyes, and the surface functional groups would be different. Where there are two or more analytes to be detected in a test sample, a number of different series (of "species") of pair of microparticles can be used, each series for a different analyte. The microparticles in different series can have same or different physical characteristics, but they should be distinguishable in cytometry in terms of their internal reference signals such that the detection signals for different analytes can be properly distinguished and separated.

As used herein, the detection agent can specifically bind to or otherwise couple to the analyte and can emit detection signals in fluorescence flow cytometry or mass cytometry. The detection agent can include a binding portion and a signaling portion. The signaling portion can comprise a fluorescent label, a chemiluminescent label, a metal or atomic mass label, or a combination thereof. The binding portion can comprise an antigen, or an epitope thereof which can specifically bind to the analyte which may be an antibody. In some embodiments, the binding portion is selected from the group consisting of an immunoglobulin molecule (an antibody), the antigen binding portion of an antibody, a Fab region of an antibody, an Fc portion of an antibody, a receptor protein, an analyte ligand, or an aptamer.

The detection agent can be introduced into the mixture of the test sample and microparticles before, during or after incubation of the microparticles with the test samples containing target analytes and/or standard solutions containing known amounts of analytes.

In some embodiments, the detection agent comprises a fluorescent dye. In such embodiments, detecting the detection signals generated by the detection agent bound with each microparticle comprises detecting fluorescence signals emitted from the microparticle. In some of embodiments, the substrate of each of the microparticles comprises a fluorescent dye. In such embodiments, detecting the internal reference signals emitted by the substrate in each microparticle comprises detecting fluorescence signals emitted from the microparticle.

In some embodiments, the detection agent comprises a heavy metal ion tag. In such embodiments, detecting the detection signals generated by the detection agent bound with each microparticle comprises detecting a signal representing the heavy metal ion tag included in the detection agent in a mass spectrometer. In some embodiments, the substrate of each of the microparticles for the analyte of the N target analytes comprises a heavy metal ion tag, wherein the heavy metal ion tags in a capture microparticle and its corresponding control microparticle are different, and each being different from the heavy metal ion tag of the detection agent. In such embodiments, detecting the internal reference signals emitted by the substrate in each microparticle comprises detecting a signal representing the heavy metal ion tag included in the substrate in the mass spectrometer.

In some embodiments, the detection agent comprises a chemiluminescent dye. In such embodiments, detecting the detection signals generated by the detection agent bound with each microparticle comprises detecting a signal representing the chemiluminescent signal included in the detection agent.

In some embodiments, the detection agent comprises radioactive substance. In such embodiments, detecting the detection signals generated by the detection agent bound with each microparticle comprises detecting a signal representing the radioactive signal included in the detection agent.

In certain embodiments, the sample to be tested is a biological sample obtained from an individual, and the analyte(s) comprises a human antibody having a known isotype and specific to a known antigen. The capture agent of each pair of capture microparticles and control microparticles for the analyte comprises a capture antibody capable of binding specifically to the Fc portion of the known human antibody isotype or coupling with a receptor of Fc portion of the known human antibody isotype. The control microparticles for the analyte includes a saturating amount of a blocking antibody binding to the amount of the capture antibody available in the control microparticles, wherein the blocking antibody has the same known isotype, but is non-specific to the known antigen or is specific to an antigen that is treatment-naïve to the individual of whom the biological sample is obtained from. This way, the capture microparticles retain the capability of capturing the target analyte having the known isotype and specific to the known antigen. The detection agent for the first analyte comprises the known antigen.

In some these embodiments, the known antigen is selected from a drug or a component of a natural allergen of the target antibody. As used herein, an allergen is a substance that causes an allergic reaction in the human body. Examples of allergens include but are not limited to: pollen, grasses, dust, drugs, drug excipients, and peanut. In some of these embodiments, the capture antibody is a monoclonal or polyclonal anti-Fc antibody, such as an antibody specifically binds to an IgM, IgG (including IgG1, IgG2, IgG3), IgA (including IgA1, IgA2) or IgE. In some of these embodiments, the receptor of Fc portion can be selected from Fc-mu receptors (FcμR), Fc-gamma receptors (FcγR), Fc-alpha receptors (FcαR), Fc-alpha/mu receptor (Fcα/μR), Fc-epsilon receptors (FcεR), or FcRn.

In some embodiments, the capture antibody can be a polyclonal antibody. In other embodiments, the capture antibody can be a monoclonal antibody.

As used herein, a target analyte is an analyte that is possibly present in a sample to be tested. The target analyte may or may not be actually present in the sample. To provide a basis of correlation, the disclosed methods can be first applied to a series of standard solutions containing varying but known concentrations of the analyte(s) which are suspected to be present in the test sample(s). All the microparticles, other reagents, conditions and steps of the method are identical except that the standard solutions of the analyte are used instead of the test sample. This procedure produces reference values of detection signal difference between capture microparticles and control microparticles at each known concentrations of the analyte, and can establish relationship between calibrated weighted values derived from such signal difference and amounts of analyte possibly present in a test sample (e.g., by interpolation, or fitting or other mathematical or numerical techniques). In such a manner, a standard curve (or a calibration curve) is obtained, which can be used to determine the amounts/abundance of the analyte in a test (unknown) sample.

Multiple known concentrations of standard solutions of an analyte can be prepared by dilution or serial dilution of a known concentration of a stock standard solution containing a known amount of the analyte. The stock solution can be prepared based on the type of biological sample to be analyzed or electrolyte buffer (e.g., phosphate buffered saline, PBS). For example, if a test sample is a urine sample, PBS sample can be used as the stock standard solution with the specific amounts of a target analyte spiked therein. If the test sample is plasma or serum from a blood sample, PBS or pooled human sera can be used as the stock standard solution with the specific amounts of a target analyte spiked therein. In the case when normal pooled sera are used as the stock standard solution, it should be validated that there are no target analytes pre-existing in the stock standard solution, though background binding is allowed as it will be canceled in data analysis.

When there are two or more target analytes to be detected in a test sample, standard solutions containing analytes of known concentrations corresponding to each of the target analytes can be utilized, and a calibration curve for each of the analytes can be constructed for the quantification of respective analytes in the test sample.

As used herein, a weighted value from the obtained detection signals of the capture microparticles and control microparticles can be a median or mean value of the respective detection signal (raw signal) of respective types of microparticles. Raw data from flow cytometry can be displayed intuitively as histograms, showing the distribution of the number of individual detection signals. In a normal distribution, the mean and median are the same.

In some embodiments, the disclosed methods can be used to determine the presence or absence of an analyte (without quantifying the analyte) without referencing a standard curve of such an analyte. Instead, this determination can be based upon a statistical analysis of the signal difference between the capture microparticles and corresponding control microparticles. For example, to conduct statistical analysis using t-test, first set the hypothesis:

Null Hypothesis: On average, detection signals of the capture microparticles will not have any more weighted signal than detection signals of the corresponding control microparticles; or Alternative Hypothesis: On average, detection signals of the capture microparticles will have more weighted signal than detection signals of the corresponding control microparticles. Then calculate average $\overline{X}_{Cap}$ and $\overline{X}_{Ctrl}$, standard deviation $\mu_{Cap}$ and $\mu_{Ctrl}$ (for Null hypothesis, $\mu_{Cap}=\mu_{Ctrl}$), standard error ($SE(\overline{X}_{Cap}-\overline{X}_{Ctrl})$) of the detection signals of two microparticle populations. Calculate t value using formula:

$$t = \frac{(\overline{X}_{Cap} - \overline{X}_{Ctrl}) - (\mu_{Cap} - \mu_{Ctrl})}{SE_{(\overline{X}_{Cap} - \overline{X}_{Ctrl})}}.$$

Evaluate the t-test statistic with the critical value from the t-distribution at (n1+n2−2) degrees of freedom (n1 is the repeating number of capture microparticles, n2 is the repeating number of control microparticles). Using t Table to find the P-value. If $P<0.05$, more preferably $P<0.01$, or more preferably, $P<0.001$, even more preferably $P<0.0001$ or more, reject the null hypothesis and accept the alternative hypothesis, i.e., detection signals of the capture microparticles have more weighted signal than detection signals of the corresponding control microparticles, the corresponding analyte is positive (determined to be present). Otherwise, if $p>0.05$, accept the null hypothesis, i.e., there is no significant difference of the detection signals between the capture and control microparticles, the corresponding analyte is negative (determined as being absent) in the sample. The calculation and hypothesis testing can be conducted by statistics software (e.g., SPSS, SAS, JMP) based upon raw data or more practically, using flow cytometry analysis software such as FlowJo. The choices and application of such statistical analysis are within the skills of artisans in the art.

In some embodiments, when there are two or more target analytes to be detected in a sample, the detection agent for one analyte is different from the detection agent for another analyte. In other embodiments, the detection agent for each of the N target analytes are the same.

In some embodiments, when there are two or more target analytes to be detected in a sample, the substrate included in the capture microparticles for one analyte of the N target analytes emits different internal reference signals than the substrate included in the capture microparticles for another analyte of the N target analytes. In some embodiments, the substrate included in the control microparticles for one analyte of the N target analytes emits different internal reference signals than the substrate included in the control microparticles for another analyte of the N target analytes. For example, to detect three target analytes in a sample, three pairs and six different types of microparticles can be used, e.g., (I, I-Ctrl), (II, II-Ctrl), (III, III-Ctrl), where the substrate for each of the six different types of microparticles emit internal reference signals different from any other types of microparticles.

In the described methods, it is understood when the capture microparticles and control microparticles are mixed with a test sample, the mixing is performed under suitable conditions (e.g., temperature/duration, stirring, or other mixing conditions) that allow binding between the analyte(s) and the microparticles. Also, the detection agents are added in suitable conditions to allow binding between the analytes and the detection agent. The choices of such conditions are within the skills of artisans in the art.

As the non-specific binding signals can be removed by using the control microparticles and removing the effects of non-specific binding signals, the disclosed method is self-calibrated, leading to high specificity, high sensitivity and high accuracy/precision in terms of detecting target analytes. Also, once the capture microparticles and corresponding control microparticles have been prepared, they can be pooled in a 1:1 ratio together for all downstream operations. This can minimize the operation errors and system errors for downstream operations. Also, the disclosed methods allow a wide range of sample volume. In all these aspects, they are superior than the current immunoassays (e.g., ELISA, ImmunoCAP, or microarray).

EXAMPLES

The following examples are to illustrate, but not limited to, the claimed invention.

Example 1: Detection of an Anti-PEG Antibody in Serum

Mouse immunized serum: Leading Life Technology, obtained through CRO
Capture bead: CBA B4-PEG (prepared by LLT)
Associated control bead: CBA B8-BSA (LLT)
Samples: PEG-immunized mouse serum sample (CRO of LLT)
Analytes: anti-PEG Igs in mouse serum
Detection agent: PE-labeled goat anti-mouse Igs, IgG polyclonal (BD Biosciences)

Figure 1A:
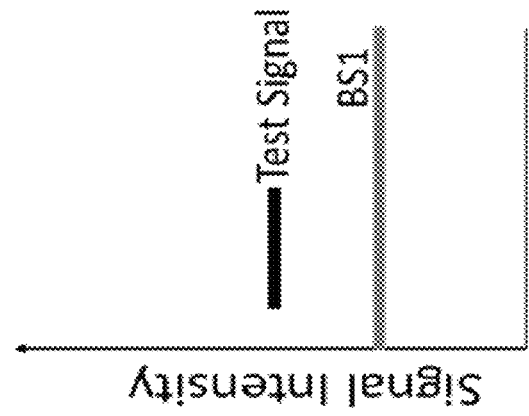
FIGS. 1A, 1B, and 1C shows in a ligand binding assay, background binding signal (B.S.) determines the assay cut point, or limit of detection (LOD).
Figure 1B:
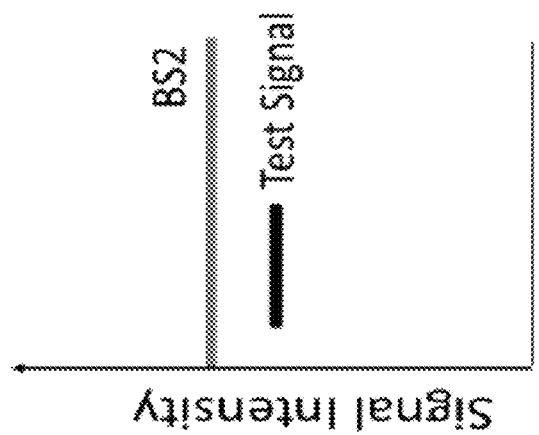
Figure 1C:
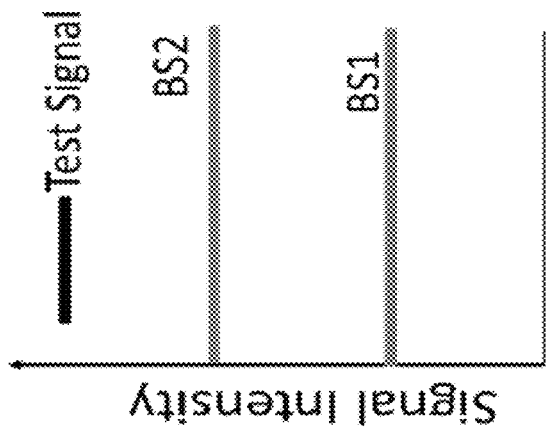
Figure 2A:
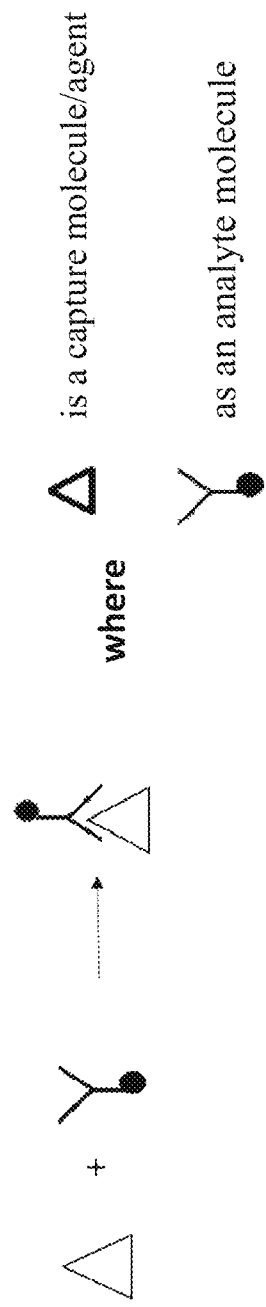
Figure 2B:
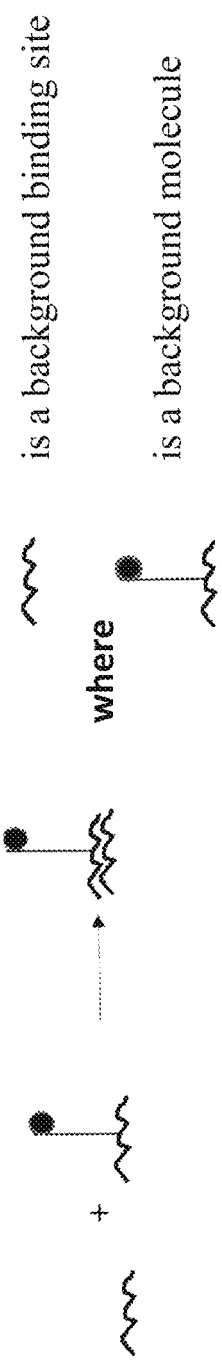
Figure 2H:
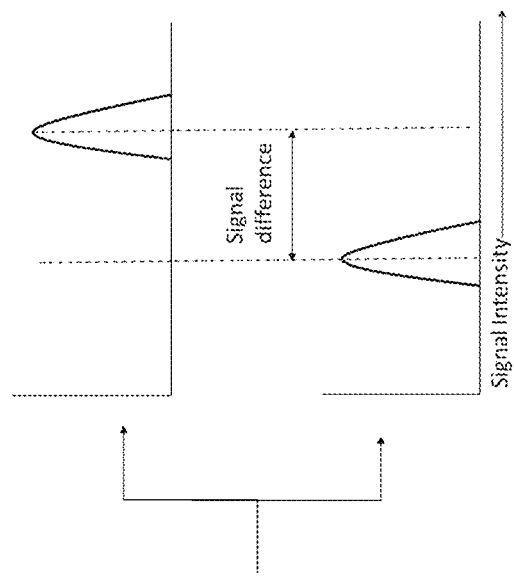
Figure 2G:
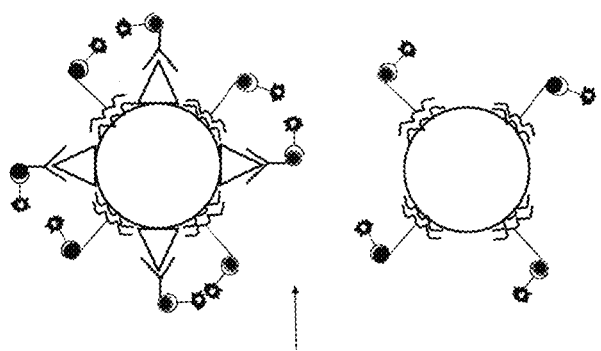
Figure 3F:
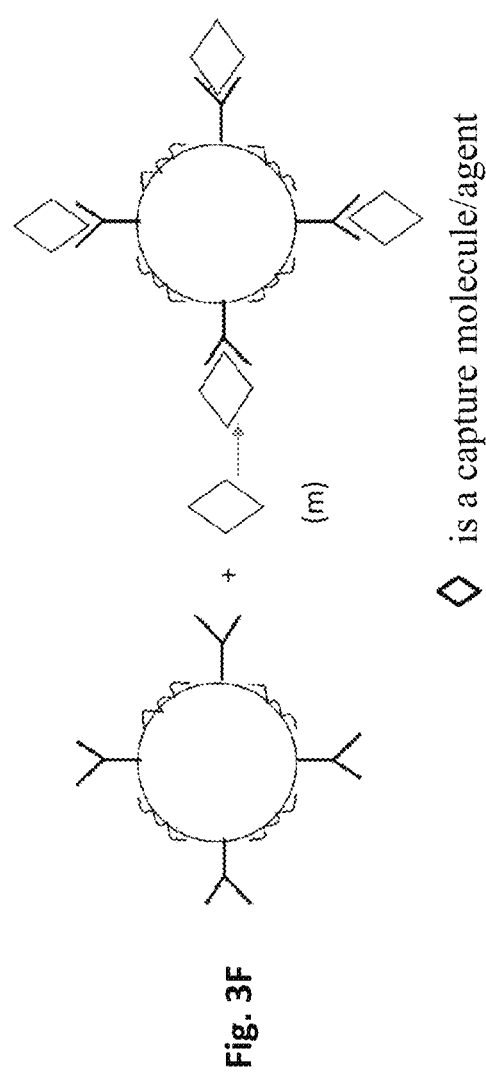
Figure 3G:
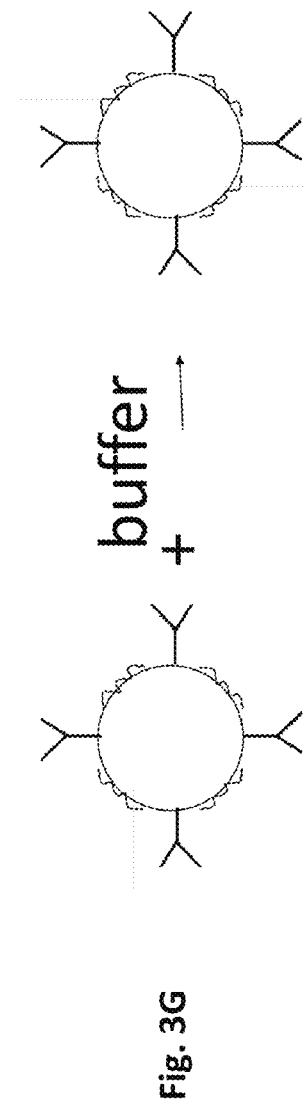
Figure 4B:
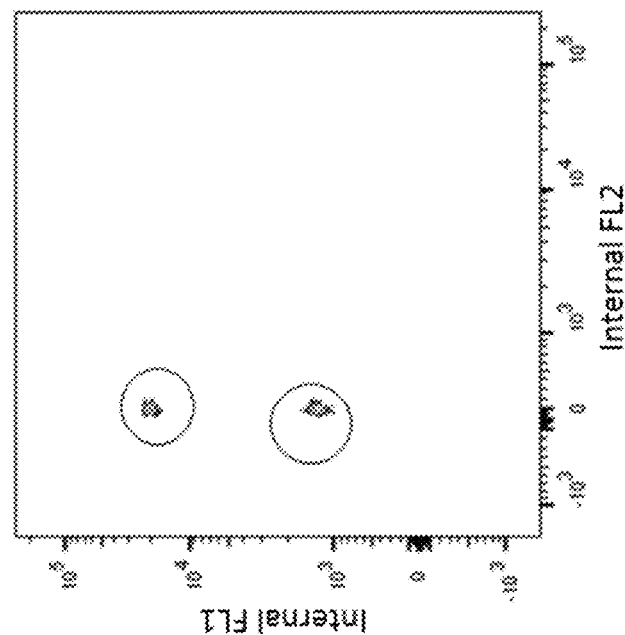
Figure 4A:
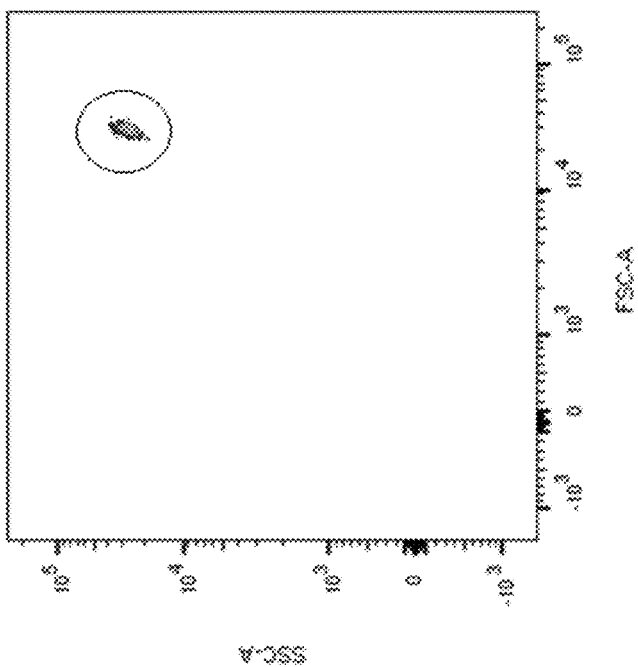
Figure 4D:
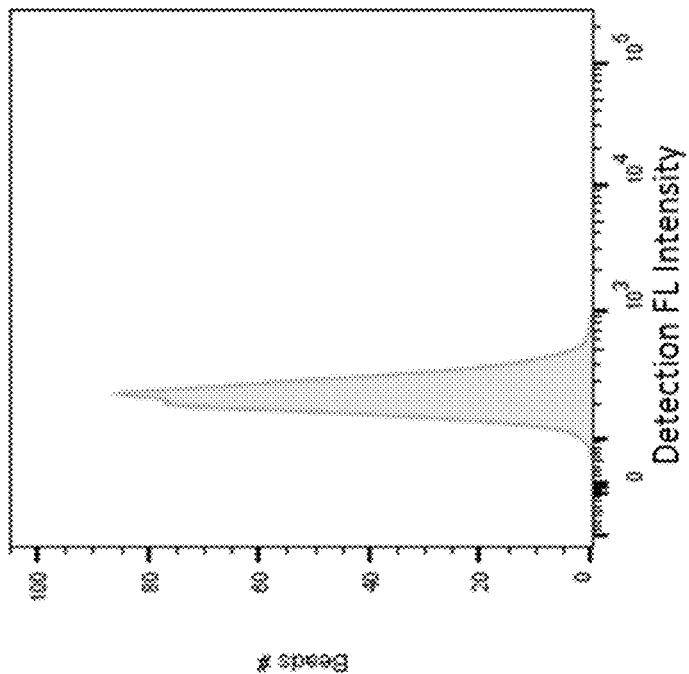
Figure 4C:
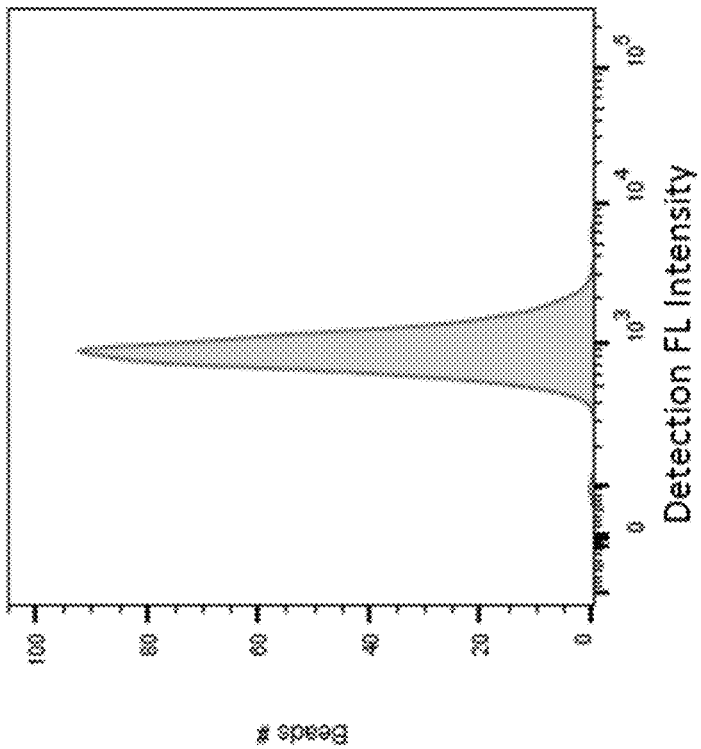

Polyethylene glycol (PEG) immunized mouse serum was collected and tested for mouse anti-PEG antibody titer using a pair of capture microparticles and corresponding control microparticles. Capture microparticles were made by conjugating 20KD PEG with CBA B4 beads (purchased from BD Biosciences, San Jose, Calif.) as illustrated in FIG. 2E; the corresponding control microparticles were made by conjugating BSA with CBA B8 beads (BD Biosciences) as illustrated in FIG. 2E. B4 and B8 beads are the same size, indistinguishable by FSC and SSC by flow cytometry, i.e., showed as the same region in the FSC-SSC plot (FIG. 4A), but are distinguished by internal fluorescence (FIG. 4B.). Capture microparticles and the corresponding control microparticles were mixed by 1:1 ratio, incubated with blocking buffer, i.e., pH 7.4 PBS containing 2% BSA (PBS-BSA) for 30 mins at room temperature. The immunized mouse serum is first diluted by 1:80, followed by serial dilution by a factor of 2. The mixed capture microparticles and control microparticles were then added to the diluted serum and incubated for 2 hours at room temperature. The beads were then washed twice with PBS-BSA by centrifugation. The test samples were added with PE-labeled goat anti-mouse Ig (BD Biosciences) 1:50 dilution, and incubated at room temperature with shaking for 1 hour, washed twice with PBS-BSA by centrifugation. The fluorescence intensity of the test samples were detected by fluorescence flow cytometer.

Figure 4F:
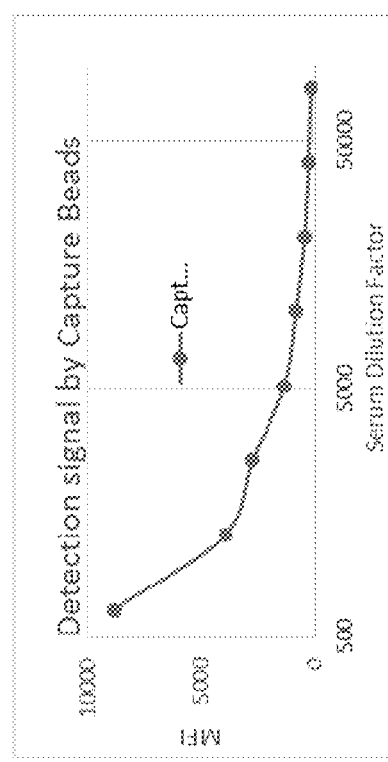
Figure 4G:
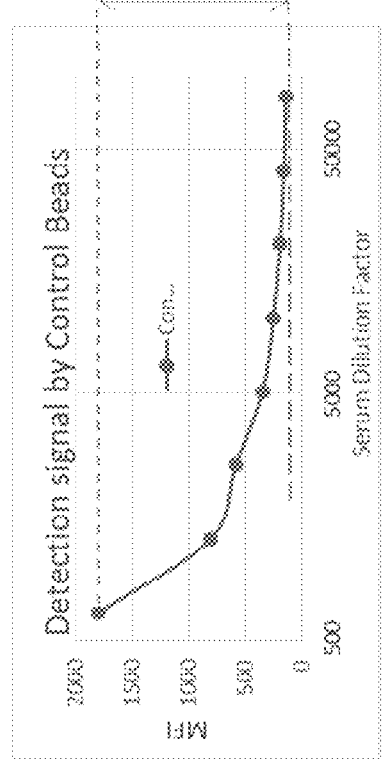
Figure 4H:
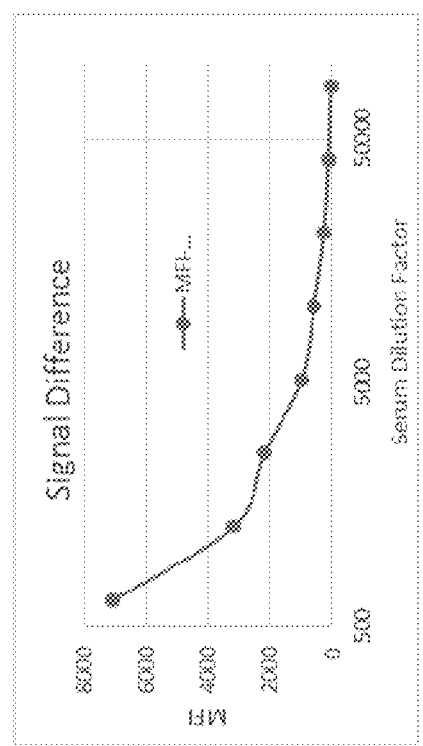
Figure 5F:
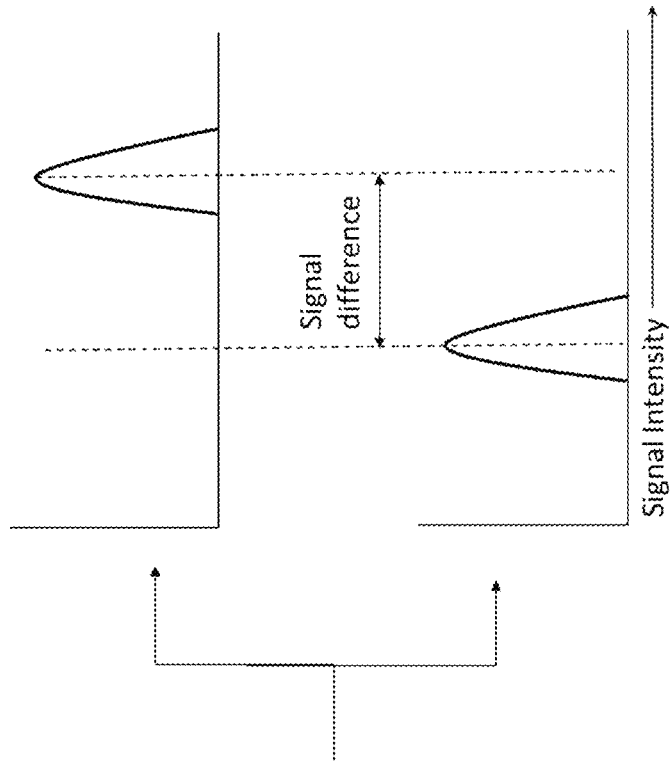
Figure 5E:
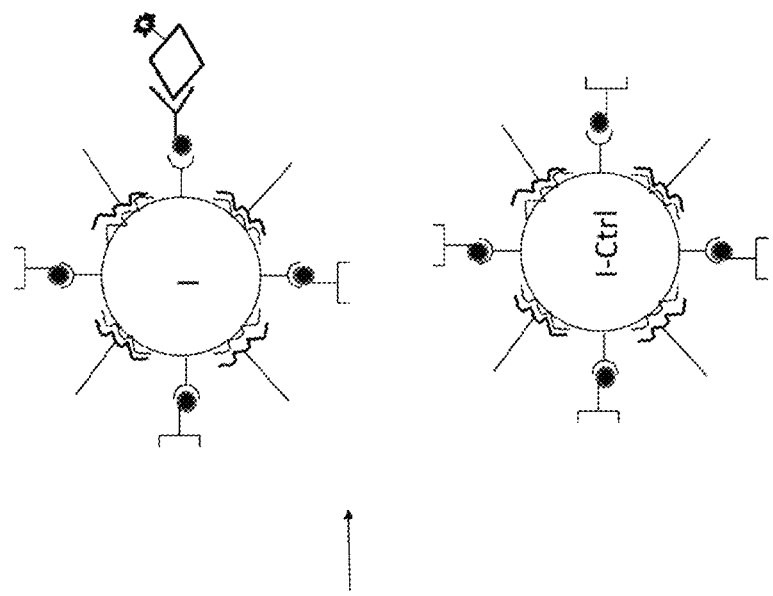
Figure 7E:
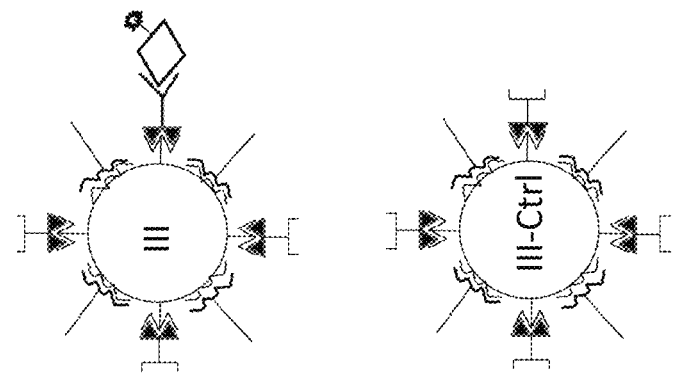
Figure 7F:
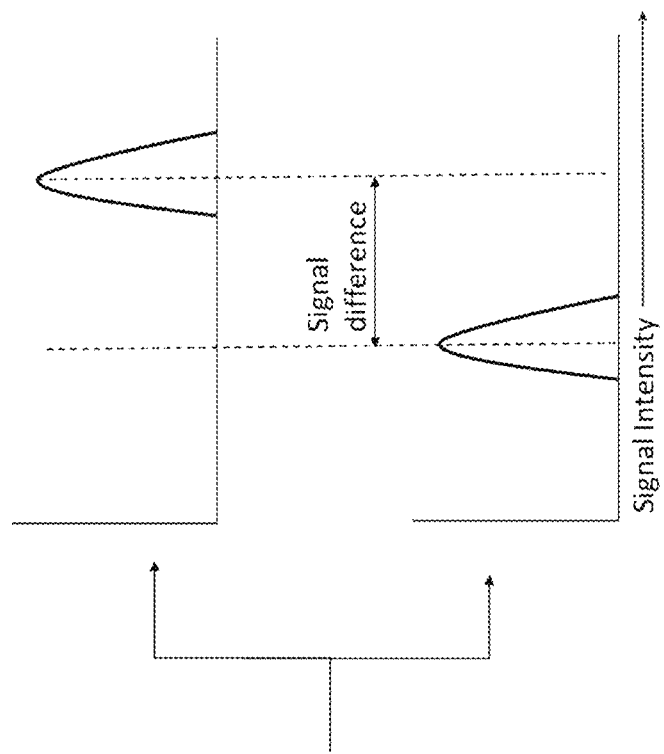
Figure 8A:
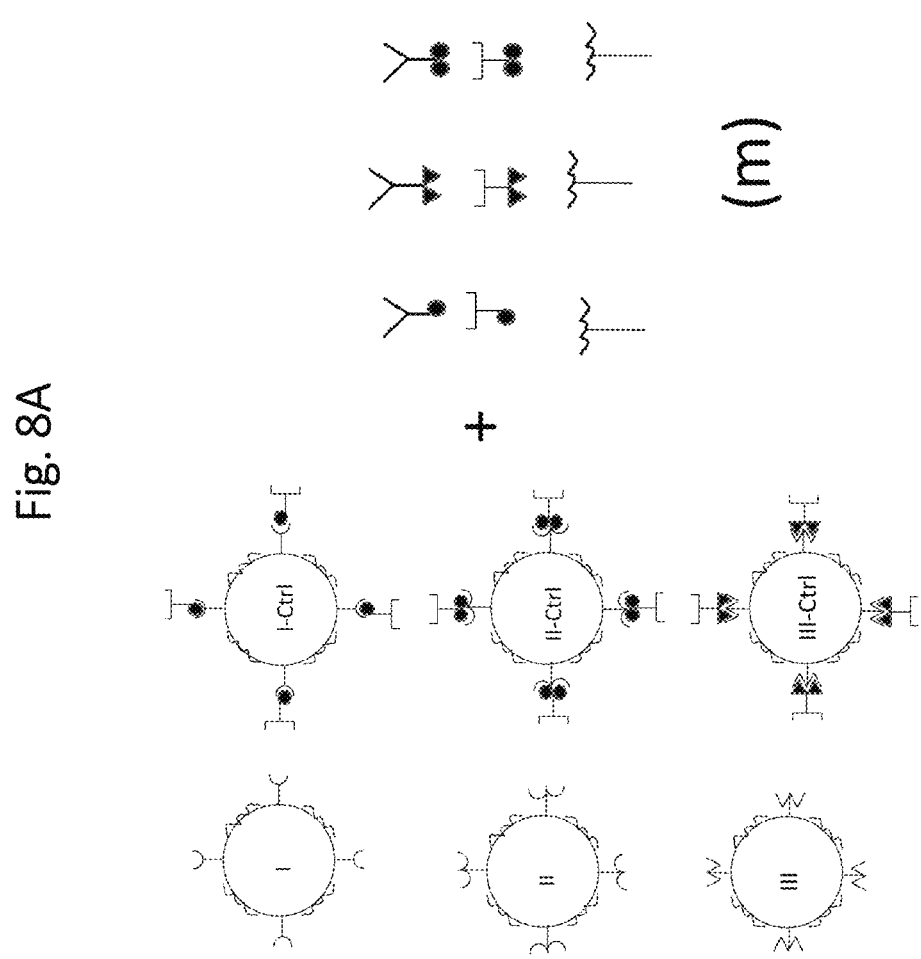
FIGS. 8A-8D illustrate a work flow using a mixture of the three series of pairs of capture microparticles and the corresponding control microparticles previously illustrated in connection with FIGS. 5A-5E, FIGS. 6A-6E, FIGS. 7A-7E to detect the three analytes simultaneously. The capture microparticles but not the control microparticles can capture different isotypes of analytes through the specific anti-isotype antibodies (or specific isotype receptors) carried by the microparticles, and further bind with labeled antigens (detection agent, e.g., fluorochrome-labeled for fluorescence flow cytometry or metal-tagged for mass cytometry). After signal detection by fluorescence flow cytometry or mass cytometry, background binding signal can be removed by subtracting the signal of the corresponding control microparticles from that of the capture microparticles, and signal difference for each series of pairs microparticles can be calculated to detect the presence and quantify the amounts of the three analytes.
Figure 8B:
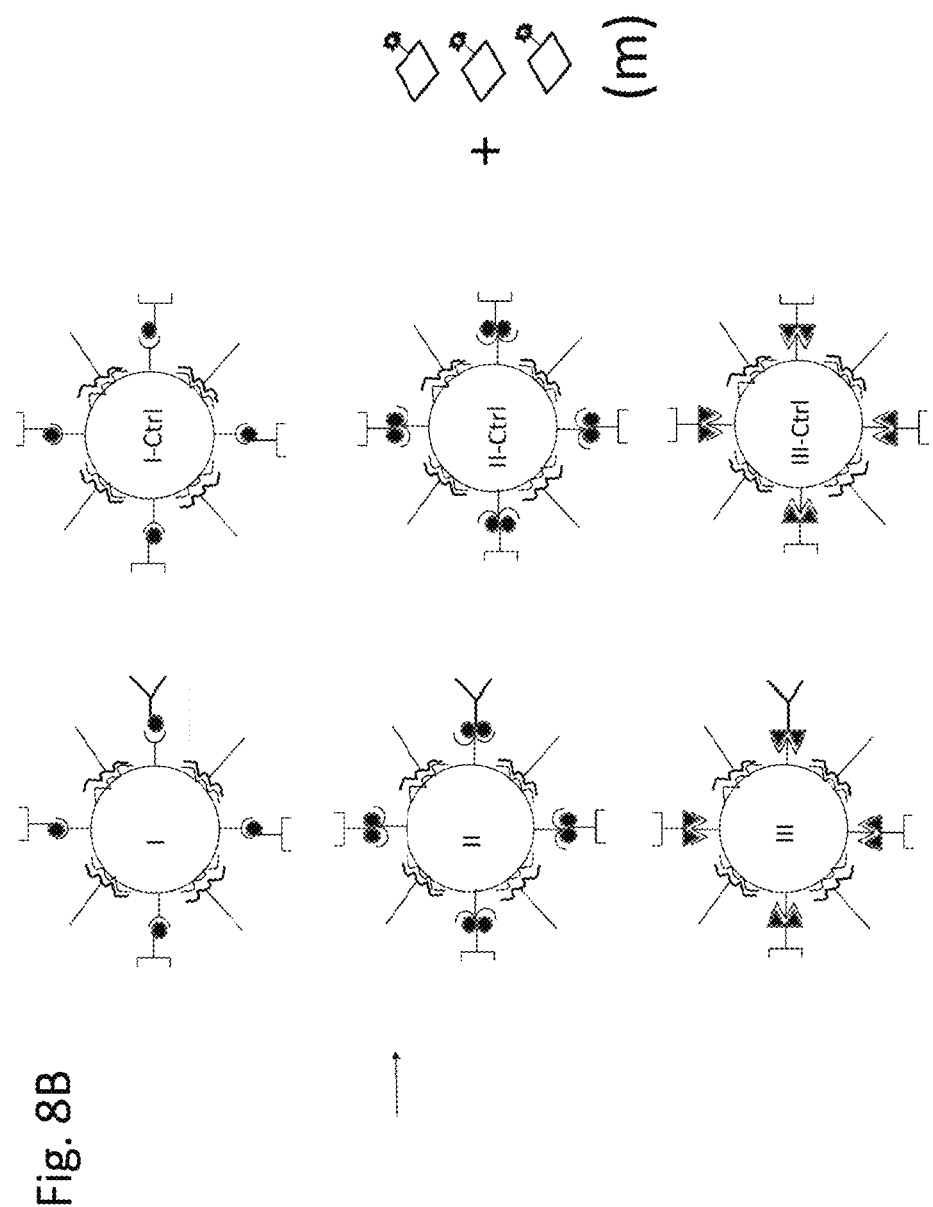
Figure 8C:
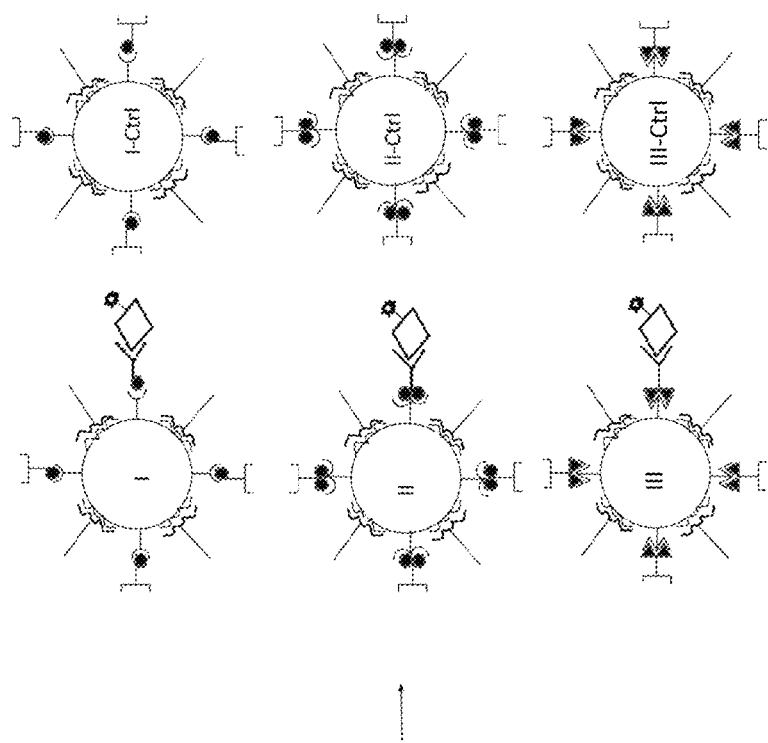
Figure 8D:
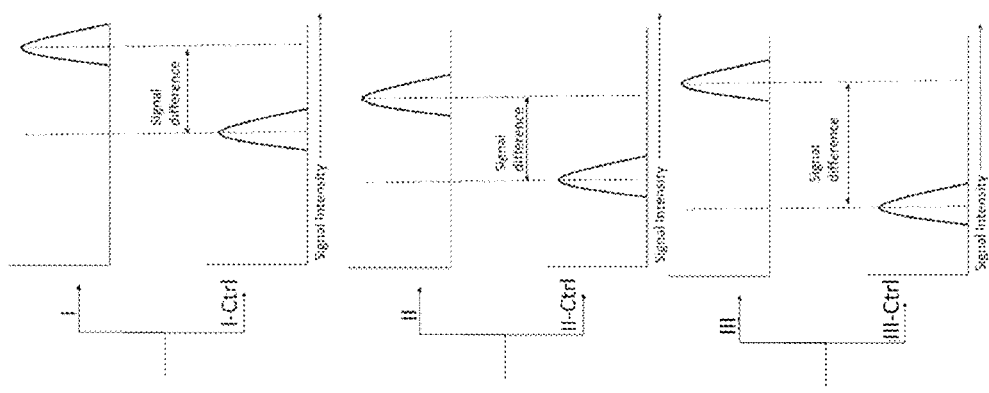

As shown in FIG. 4F and FIG. 4G, both capture microparticles and control microparticles show a titration dependent fluorescence intensity trend. The control microparticles trend indicates the background binding is different at different concentrations. The capture microparticles signal includes specific anti-PEG Ig binding as well as the background binding signal, the specific binding signal is calculated by subtraction of background signal (signal obtained from control microparticles) from the signal of the capture microparticles, as shown in FIG. 4H. This self-calibration method can cancel the background noise (aka noise canceling), therefore the specificity and sensitivity of the detection are greatly improved.

The control microparticle trend indicates of background binding is different at different titration with the cut point range indicated (FIG. 4G, about 100 to 1700 intensity unit). Suppose there were no control microparticles prepared and added in to the assay, the cut point could be set by the capture microparticles only incubated with a "negative sample" or with buffer only, in which case it might be set at any point within the cut point range as shown in FIG. 4G. (Assuming the "negative sample" with a background at any level between buffer only and the test sample). This may lead to an artificially high or low cut point setting and wrong result. The capture bead signal includes specific anti-PEG Ig binding as well as the background binding signal, the specific binding signal is calculated by subtraction of background signal from the signal of the capture bead at each independent titration point, as shown in FIG. 4H reflecting the true cut point setup and true analyte binding signal. This demonstrates the self-calibration method of this invention can cancel the background noise correctly (aka noise canceling), therefore the specificity and sensitivity and precision are greatly improved.

Example 2: Detection of Human Anti-PEG IgG, IgM and IgE Isotype (Chimeric Anti-Human IgG, IgM and IgE Detection)

Microparticles (CBA beads and conjugation buffer were purchased from BD Biosciences): Capture microparticle 1, E4-IgE, CBA bead E4 conjugated with anti-human IgE; associated control microparticle 1, B4-IgE, CBA bead B4 conjugated with anti-human IgE. The conjugation of capture bead 1 and the associated control bead 1 with IgE are processed with the same procedure including anti-IgE dosage. The FSC and SSC of the two microparticles are indistinguishable (FIG. 9A).

Capture microparticle 2, E6-IgM, CBA bead E6 conjugated with anti-human IgM; associate control microparticle 2, B6-IgM, CBA bead B6 conjugated with anti-human IgM. The conjugation of capture bead 2 and the associated control bead 2 with IgM are processed with the same procedure including anti-IgM dosage, the FSC and SSC of the two beads are indistinguishable (FIG. 9A).

Capture microparticle 3, E8-IgG, CBA bead E8 conjugated with anti-human IgG; associate control microparticle 3, B8-IgG, CBA bead B8 conjugated with anti-human IgG. The conjugation of capture bead 3 and the associated control bead 3 with IgG are processed with the same procedure including anti-IgG dosage, the FSC and SSC of the two beads are indistinguishable (FIG. 9A).

Using anti-mouse Ig secondary antibody revealed the conjugation of mouse anti-human Ig on both capture bead and control bead of each pair with the same fluorescence intensity.

Samples: Different dilution of chimeric mouse anti-PEG antibodies with human Ig Fcs (i.e., IgM, IgG, IgE), were obtained through and/or prepared at Leading Life Technologies (LLT) (CA, USA).

Analytes: anti-PEG IgG, anti-PEG-IgM, anti-PEG IgE (LLT)

Detection agent: PE-labeled PEG (LLT)

None specific human IgM, IgG and IgE were purchased from Sigma.

Associated control bead 1 ($10^5$ beads in 100 uL PBS-BSA) were incubated with non-specific IgE (20 µg) at room temperature (RT) for 1 h; Associated control bead 2 ($10^5$ beads in 100 uL PBS-BSA) were incubated with non-specific IgM (20 µg) at RT for 1 h; Associated control bead 3 ($10^5$ beads in 100 uL PBS-BSA) were incubated with non-specific IgG (20 µg) at RT for 1 h;

Wash, and mix with capture microparticles, add separately or mix together, and add into a different dilution of samples, incubate at cold overnight, and wash twice with PBS-BSA. Add PE-labeled PEG 5 uL per test, incubate at RT for 2 hours, wash and detection by BD flow cytometer.

Result: Background (matrix) binding as shown by detection fluorescence signal of the control microparticles of each respective pair (FIG. 9C, histogram in blue color for IgE, IgM, and IgG, respectively). Capture microparticles (FIG. 9C, histogram in red color for IgE, IgM, IgG, respectively) show binding signal containing background and analyte binding signals. The fluorescence difference between capture microparticles and the associated control microparticles reveal the true specific binding and correlate with the amount of analyte in the test samples (FIG. 9C signal difference).

Example 3: Detection of Anti-PEG Antibody in Serum by Mass Cytometry

Chimeric human anti-PEG IgG (Leading Life Technology, purchased from Institute of Biomedical Sciences Academia Sinica, Taiwen)

Capture microparticle: 174Yb-tagged anti-PEG microparticle named "CBA B4-Anti-PEG-174Yb", made by CBA B4 beads coupled with Anti-Mouse I-A/I-E (M5/114.15.2)-

174Yb (Fluidigm, CA) and a mouse anti-PEG monoclonal antibody (prepared by Life Diagnostics, Inc., West Chester, Pa.).

Corresponding control microparticle: 209Bi-tagged anti-PEG microparticle named "CBA B8-Anti-PEG-209Bi", made by CBA B8 beads coupled with Anti-Mouse I-A/I-E (M5/114.15.2)-209Bi (Fluidigm, CA) and a mouse anti-PEG monoclonal antibody (Life Diagnostics, Inc., West Chester, Pa.).

The particle size, amount of surface-coupled anti-mouse I-A/I-E and anti-PEG antibody were validated to be the same for capture microparticle and associated control microparticle.

Samples: 1 µg and 0.5 µg of chimeric human anti-PEG IgG were diluted, respectively, in two different human sera with different background.

Analytes: human anti-PEG IgG.

Detection agent: Anti-human IgG-145Nd (Fluidigm, CA) $1\times10^5$ capture microparticles were incubated with 1.5 µL, of PEG (Pegloticase, 80 mg/mL) in 200 uL PBS containing 2% BSA and 2 mM EDTA (buffer), while $1\times10^5$ corresponding control microparticles were incubated with buffer, respectively, for 1 hour. After washing with PBS buffer and centrifugation (900 g×3 minutes) for 5 times, respectively, capture microparticles and associated control microparticles were mixed and allotted into test samples. After further incubation at 4 degree for two hours with shaking, the sample-microparticles mixture were washed with buffer twice. Added with 1 test/20 µL of detection agent in 200 µL of buffer, incubated at room temperature with shaking for 1 hour. After washing, the samples were analyzed by a mass cytometer CyTOF (Fluidigm). The CyTOF data were analyzed by FlowJo software. The separation of capture microparticles and corresponding control microparticles were based upon tagged-metals, followed with analysis of detection signal on the capture microparticles and corresponding control microparticles.

As shown in FIGS. 10A and 10C, signals from capture microparticles and control microparticles can be separated based upon mass signal of tagged metal 174Yb and 209Bi. The detection signal of mass 145Nd is related to anti-human IgG, including analyte (i.e., anti-human PEG IgG) and non-specific human IgG binding. As shown in FIG. 10B and FIG. 10D, two different human serum samples with added analyte exhibited different background binding signal as revealed by the control microparticles (blue histogram). The detection signal difference between capture microparticles and the associated control microparticles reveal the true specific binding and correlate with the amount of analyte in the test samples.

As used herein, the term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

The disclosures of all publications, patents, patent applications and published patent applications referred to herein by an identifying citation are hereby incorporated herein by reference in their entirety.

Although various embodiments have been described by way of illustration and example for purposes of clarity of understanding, it is apparent to those skilled in the art that changes and modifications can be made without departing from the scope and spirit of the present disclosure. The description and examples herein should not be construed as limiting the scope of the invention.

What is claimed is:

1. A method for detecting N target analytes which may be present in a sample, N being a natural number equal to or greater than 1, the method comprising:
   (a) to the sample, for each analyte of the N target analytes: adding a plurality pairs of microparticles, each pair comprising (1) a capture microparticle and (2) a corresponding control microparticle, to thereby form a mixture; wherein the capture microparticles each comprise a first substrate and a first capture agent coupled thereon, the first capture agent being unblocked and capable of specifically binding to the analyte; wherein the control microparticles each comprise a second substrate coupled with a second capture agent, the second capture agent being the same as the first capture agent, but being blocked by a blocking agent and incapable of specifically binding to the analyte;
   (b) to the mixture, for each analyte of the N target analytes, adding a detection agent capable of binding to the analyte;
   (c) aligning and passing each of the plurality of pairs of microparticles for each of the N target analytes in a single file in a flow cytometer while detecting (1) detection signals generated by the detection agent bound with each microparticle, and (2) internal reference signals emitted by the first or second substrate in each microparticle; wherein the internal reference signals of the capture microparticles and of the corresponding control microparticles are different and distinguishably distinct from each other, and are each different from the detection signals;
   (d) for each of the N target analytes in step (c), distinguishing the detection signals from the capture microparticles and detection signals from corresponding control microparticles based on the different internal reference signals detected;
   (e) for each of the N target analytes in step (d), obtaining a first weighted value reflecting signal intensity of the obtained detection signals of the capture microparticles and a second weighted value reflecting signal intensity of the obtained detection signals from the corresponding control microparticles, and subtracting the second weighted value from the first weighted value to obtain a calibrated weighted value; and
   (f) for each analyte of the N target analytes in step (e), determining the abundance of the analyte in the sample based on the calibrated weighted value.

2. The method of claim 1, wherein the detection agent comprises a fluorescent dye, wherein detecting the detection signals generated by the detection agent bound with each microparticle comprises detecting fluorescence signals emitted from the microparticle.

3. The method of claim 2, wherein the substrate of each of the microparticles comprises a fluorescent dye, and detecting the internal reference signals emitted by the substrate in each microparticle comprises detecting fluorescence signals emitted from the microparticle.

4. The method of claim 1, wherein the detection agent comprises a heavy metal ion tag, wherein detecting the detection signals generated by the detection agent bound with each microparticle comprises detecting a signal representing the heavy metal ion tag included in the detection agent in a mass spectrometer.

5. The method of claim 4, wherein the substrate of each of the microparticles for each analyte of the N target analytes comprises a heavy metal ion tag, wherein the heavy metal ion tags in each pair of the microparticles for any analyte of the N target analytes are different from each other and each different from the heavy metal ion tag of the detection agent, wherein detecting the internal reference signals emitted by the substrate in each microparticle comprises detecting a signal representing the heavy metal ion tag included in the substrate in the mass spectrometer.

6. The method of claim 1, wherein each of the N target analytes comprise an antibody or biotinylated antibody specific to an antigen or allergen.

7. The method of claim 6, wherein the antigen or allergen is selected from the group consisting of a protein, a bacteria or a bacteria component thereof, a virus or a virus component, a toxin, a drug or a drug excipient, pollen, grass, dust and peanut.

8. The method of claim 1, wherein each of the N target analytes is independently selected from the group consisting of a pharmaceutical compound, a factor in blood, a protein, a bacteria or a bacteria component thereof, a virus or a virus component, a peptide, an antibody, a toxin, a hormone, a cytokine, an immunoglobulin or the Fab portion thereof, a polynucleotide, and a drug carrier or excipient.

9. The method of claim 1, wherein the sample comprises a bodily fluid or biotinylated bodily fluid.

10. The method of claim 9, wherein the bodily fluid is selected from the group consisting of blood, plasma, serum, urine, saliva, mucosal secretions, nasopharyngeal and oropharyngeal swabs, respiratory sputum, snivel tears and tissue lysate.

11. The method of claim 1, wherein the first or second capture agent comprises an antigen or antibody.

12. The method of claim 11, wherein the antigen is selected from the group consisting of a protein or a peptide, a bacteria or a component thereof, a virus or a component thereof, a toxin, a hormone, a cytokine, a pharmaceutical compound, a blood factor, an immunoglobulin or the Fab portion thereof, a polynucleotide, a drug carrier or excipient, a food allergen or a seasonal allergen.

13. The method of claim 1, wherein determining the abundance of the analyte comprises detecting the presence or absence of the analyte.

14. The method of claim 1, wherein the sample is a biological sample obtained from a human individual, wherein a first analyte of the N target analytes is a human antibody having a known isotype and specific to a known antigen, wherein the first and second capture agent of each pair of microparticles and control microparticles for the first analyte comprises a capture antibody capable of binding specifically to the Fc portion of the known human antibody isotype or coupling with a receptor of Fc portion of the known human antibody isotype; further wherein the block agent blocking the second capture agent in the control microparticles for the first analyte includes a blocking antibody or the Fc portion thereof binding to the capture antibody in the control microparticles, wherein the blocking antibody has the same known isotype, is non-specific to the known antigen or is specific to an antigen that has not been previously exposed to the individual from whom the biological sample is obtained; and further wherein the detection agent for the first analyte comprises the known antigen.

15. The method of claim 14, wherein the known antigen is selected from a drug or a component of a natural allergen.

16. The method of claim 14, wherein the capture antibody is a monoclonal or polyclonal anti-Fc antibody.

17. The method of claim 16, wherein the anti-Fc antibody is an antibody specifically binds to IgG, IgA, IgM, or IgE.

18. The method of claim 14, wherein the receptor of Fc portion is Fc-mu receptors (FcμR), Fc-gamma receptors (FcγR), Fc-alpha receptors (FcαR), Fc-alpha/mu receptor (Fcα/μR), Fc-epsilon receptors (FcεR), or FcRn.

19. The method of claim 1, wherein in (f) the determination comprises, for each analyte of the N target analytes:
using a plurality of standard samples of varying known concentrations of the analyte which are mixed with the same pair of microparticles in (a) and with the same amounts for the same analyte and processed with the steps b)-e) to generate a series of calibrated weighted values corresponding to the varying known concentrations, respectively;
obtaining a mathematical relationship between the calibrated weighted values and known concentrations of the analyte in the plurality of standard samples; and
determining the abundance of the analyte in the sample based on the obtained calibrated weighted value of the analyte and the mathematical relationship.

20. The method of claim 1, wherein N is greater than 1, wherein the detection agent for one analyte of the N target analytes is different from the detection agent for another analyte of the N target analytes.

21. The method of claim 1, wherein N is greater than 1, wherein the detection agent for each of the N target analytes are the same.

22. The method of claim 1, wherein N is greater than 1, and the first substrate included in the capture microparticles for one analyte of the N target analytes emits different internal reference signals than the first substrate included in the capture microparticles for another analyte of the N target analytes.

23. The method of claim 1, wherein N is greater than 1, and the second substrate included in the control microparticles for one analyte of the N target analytes emits different internal reference signals than the second substrate included in the control microparticles for another analyte of the N target analytes.

* * * * *